(12) United States Patent
Wyndham et al.

(10) Patent No.: US 9,925,521 B2
(45) Date of Patent: Mar. 27, 2018

(54) CHROMATOGRAPHIC MATERIALS

(71) Applicant: Waters Technologies Corporation, Milford, MA (US)

(72) Inventors: Kevin D. Wyndham, Upton, MA (US); Michael F. Morris, Ashland, MA (US); Darryl W. Brousmiche, Grafton, MA (US); Jason F. Hill, Milford, MA (US); Jacob N. Fairchild, Upton, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 14/401,385

(22) PCT Filed: May 15, 2013

(86) PCT No.: PCT/US2013/041221
§ 371 (c)(1),
(2) Date: Nov. 14, 2014

(87) PCT Pub. No.: WO2013/173501
PCT Pub. Date: Nov. 21, 2013

(65) Prior Publication Data
US 2015/0133294 A1 May 14, 2015

Related U.S. Application Data

(60) Provisional application No. 61/647,303, filed on May 15, 2012.

(51) Int. Cl.
*B01J 20/32* (2006.01)
*B01J 20/282* (2006.01)
(Continued)

(52) U.S. Cl.
CPC ............ *B01J 20/283* (2013.01); *B01D 15/26* (2013.01); *B01D 15/30* (2013.01); *B01D 15/305* (2013.01);
(Continued)

(58) Field of Classification Search
None
See application file for complete search history.

(56) References Cited

U.S. PATENT DOCUMENTS 4,017,528 A  4/1977 Unger et al.
4,415,631 A  11/1983 Schutijser
(Continued)

FOREIGN PATENT DOCUMENTS

WO  WO-2008/103423 A1  8/2008
WO  2011/017418       2/2011
WO  WO-2011/017418 A1 2/2011

OTHER PUBLICATIONS

Chen et al., "Factors that Influence the Cutaneous Synthesis and Dietary Sournces of Vitamin D", Archives of Biochemistry and Biophysics, 2007, vol. 460, pp. 213-217.
(Continued)

*Primary Examiner* — Katherine Zalasky
*Assistant Examiner* — Kara Graber
(74) *Attorney, Agent, or Firm* — Womble Bond Dickinson (US) LLP; Deborah M. Vernon; Rebecca N. Barnes

(57) ABSTRACT

In one aspect, the present invention provides a chromatographic stationary phase material for various different modes of chromatography represented by Formula 1: $[X](W)_a(Q)_b(T)_c$ (Formula 1). X can be a high purity chromatographic core composition having a surface comprising a silica core material, metal oxide core material, an inorganic-organic hybrid material or a group of block copolymers thereof. W can be absent and/or can include hydrogen and/or can
(Continued)

include a hydroxyl on the surface of X. Q can be a functional group that minimizes retention variation over time (drift) under chromatographic conditions utilizing low water concentrations. T can include one or more hydrophilic, polar, ionizable, and/or charged functional groups that chromatographically interact with the analyte. Additionally, b and c can be positive numbers, with the ratio $0.05 \leq (b/c) \leq 100$, and $a \geq 0$.

2 Claims, 6 Drawing Sheets

(51) Int. Cl.

| | |
|---|---|
| B01J 20/288 | (2006.01) |
| B01J 20/283 | (2006.01) |
| B01D 15/26 | (2006.01) |
| B01J 20/28 | (2006.01) |
| B01D 15/30 | (2006.01) |
| B01D 15/32 | (2006.01) |
| B01D 15/40 | (2006.01) |
| B01D 53/02 | (2006.01) |
| B01J 20/22 | (2006.01) |
| B01J 20/289 | (2006.01) |
| C07F 7/18 | (2006.01) |
| B01J 20/30 | (2006.01) |
| B01J 20/285 | (2006.01) |
| B01J 20/284 | (2006.01) |

(52) U.S. Cl.
CPC .......... *B01D 15/322* (2013.01); *B01D 15/40* (2013.01); *B01D 53/025* (2013.01); *B01J 20/22* (2013.01); *B01J 20/28004* (2013.01); *B01J 20/288* (2013.01); *B01J 20/289* (2013.01); *B01J 20/28016* (2013.01); *B01J 20/28042* (2013.01); *B01J 20/28057* (2013.01); *B01J 20/28059* (2013.01); *B01J 20/28061* (2013.01); *B01J 20/28064* (2013.01); *B01J 20/28066* (2013.01); *B01J 20/28069* (2013.01); *B01J 20/28071* (2013.01); *B01J 20/28073* (2013.01); *B01J 20/28076* (2013.01); *B01J 20/28078* (2013.01); *B01J 20/28083* (2013.01); *B01J 20/28085* (2013.01); *B01J 20/3085* (2013.01); *B01J 20/3204* (2013.01); *B01J 20/3246* (2013.01); *B01J 20/3285* (2013.01); *B01J 20/3293* (2013.01); *C07F 7/1836* (2013.01); *B01J 20/282* (2013.01); *B01J 20/284* (2013.01); *B01J 20/285* (2013.01); *B01J 20/32* (2013.01); *B01J 20/3206* (2013.01); *B01J 20/3208* (2013.01); *B01J 20/3234* (2013.01); *B01J 2220/54* (2013.01); *B01J 2220/80* (2013.01)

(56) References Cited

U.S. PATENT DOCUMENTS

| | | | |
|---|---|---|---|
| 4,767,670 A | 8/1988 | Cox et al. | |
| 4,835,058 A * | 5/1989 | Komiya | B01J 20/3204 210/198.2 |
| 5,374,755 A | 12/1994 | Neue et al. | |
| 6,528,167 B2 | 3/2003 | O'Gara | |
| 6,686,035 B2 | 2/2004 | Jiang et al. | |
| 7,008,542 B2 | 3/2006 | Belew et al. | |
| 7,125,488 B2 | 10/2006 | Li | |
| 7,175,913 B2 | 2/2007 | O'Gara | |
| 7,250,214 B2 | 7/2007 | Walter et al. | |
| 2001/0033931 A1* | 10/2001 | Jiang | B01J 20/103 428/402 |
| 2005/0242038 A1 | 11/2005 | Chen | |
| 2006/0144770 A1 | 7/2006 | Granger et al. | |
| 2006/0207923 A1 | 9/2006 | Li | |
| 2007/0090052 A1 | 4/2007 | Broske et al. | |
| 2007/0135304 A1 | 6/2007 | Walter et al. | |
| 2007/0141325 A1 | 6/2007 | O'Gara et al. | |
| 2007/0189944 A1 | 8/2007 | Kirkland et al. | |
| 2007/0215547 A1 | 9/2007 | O'Gara | |
| 2008/0203027 A1 | 8/2008 | Liu et al. | |
| 2008/0223786 A1* | 9/2008 | Xu | B01J 20/28042 210/656 |
| 2008/0293959 A1 | 11/2008 | Liu et al. | |
| 2009/0127177 A1 | 5/2009 | Jiang et al. | |
| 2009/0209722 A1 | 8/2009 | Jiang et al. | |
| 2010/0000613 A1 | 1/2010 | King | |
| 2010/0061367 A1 | 3/2010 | Sindhu et al. | |
| 2011/0049056 A1 | 3/2011 | Wyndham et al. | |
| 2012/0055860 A1 | 3/2012 | Wyndham | |
| 2012/0273404 A1 | 11/2012 | Wyndham et al. | |
| 2013/0112605 A1 | 5/2013 | Wyndham et al. | |

OTHER PUBLICATIONS

Dermody et al., "Interactions Between Organized, Surface-Confined Monolayers and Vapor-Phase Probe Molecules. 11. Synthesis, Characteriztion, and Chemical Sensitivity of Self-Assembled Polydiacetylene/Calix[n]arene Bilayers", J.Am. Chem. Soc, 1996, vol. 118, pp. 11912-11917.
Fang et al., "Surface-Directed DNA Condensation in the Absence of Soluable Multivalent Cations", Nucleic Acids Reseaerch, 1998, vol. 26, No. 2, pp. 588-593.
Gao et al., "Immobilization of Pyrene via Diethylenetriamine on Quartz Plate Surace for Recognition of Dicarboxylic Acids", Applied Surface Science, 2006, vol. 252, pp. 3884-3893.
Kall et al.; "Determination of Total Vitamin B6 in Foods by Isocratic HPLC: a Comparions with Microbiological Analysis", Food Chemistry, 82, 2003, pp. 315-327.
Lei et al.; "Synthesis of Polymer-Supported Anthracene and Its Application s a Dienophile Scavenger", Organic Letters, 2004, vol. 6, No. 5, pp. 795-798.
Ollevier et al., "Bismuth Triflate-Catalyzed Mild and Efficient Epoxide Opening by Aromatic Amines Under Aqueous Conditions", Tetrahedron Letters, 2004, vol. 45, pp. 49-52.
International Search Report for International Application PCT/US15/17972; International Application dated Feb. 27, 2015.
Written Opinion from the International Bureau dated Jun. 8, 2015 for International Application No. PCT/US15/17972.
Porsch, B. *J. Chromatography A.* "Epoxy- and diol-mediated silica: optimization of surface bonding reaction." v. 653, pp. 1-7 (1997).
Zymor® amide, urea and pyridine phases as described on website.
Zhong et al. "Monolithic silica capillary columns having immobilized lectins and surface bound polar functionalities for lectin affinity and normal phase nano-LC and CEC of glycoconjugates, respectively" J. Sep. Sci. v. 32 pp. 1642-1653 (2009).
Gleiter, H."Nano-crystalline materials," *Prog. Mater. Sci.* v. 33, pp. 223-315 (1989).
Siegel, R. W. "Synthesis and properties of nano-phase materials," *Mater. Sci. Eng.* v. A168, pp. 189-197 (1993).
Guiochon, G. "Monolithic columns in high-performance liquid chromatography " J. Chromatogr. A. v.1168, pp. 101-168 (2007).
Massiot, D. et al. "Modelling one- and two-dimensional solid-state NMR spectra" Magn. Reson. Chem. v. 40, pp. 70-76 (2002).
Neue, U. et al. "Selectivity in reversed-phase separations: Influence of the stationary phase" J. Chromatog. A. v. 1127, pp. 161-174 (2006).
International Search Report and Written Opinion, International Application No. PCT/US2013/41221, International dated May 13, 2013.

(56) References Cited

OTHER PUBLICATIONS

International Search Report and Written Opinion, Internatioanl Application No. PCT/US2013/41207, International dated May 15, 2013.

* cited by examiner

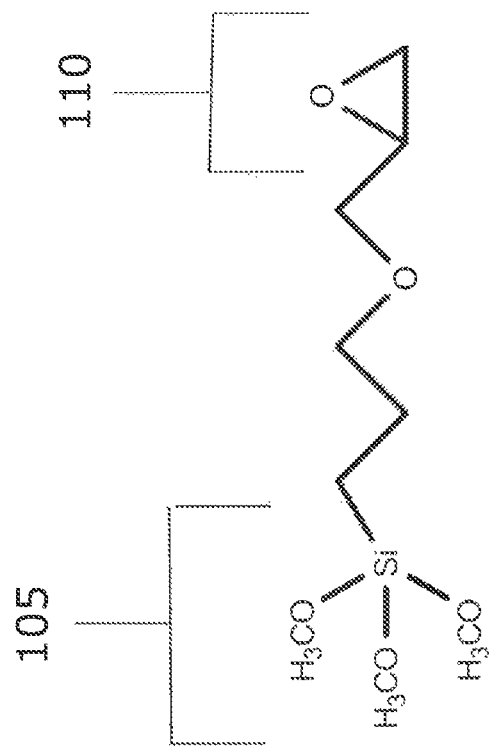
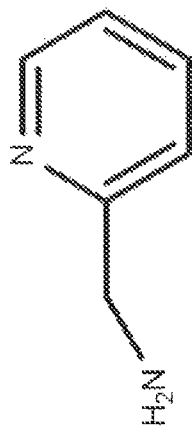
Figure 1A
Figure 1B

US 9,925,521 B2

CHROMATOGRAPHIC MATERIALS

CROSS REFERENCE TO RELATED APPLICATIONS

This application is a National Stage Application of International Application No. PCT/US2013/041221, filed May 15, 2013, which claims priority to U.S. Provisional Application No. 61/647,303 filed May 15, 2012. Each of the foregoing applications is incorporated herein by reference in its entirety.

FIELD OF THE INVENTION

The invention relates generally to chromatographic materials. The invention relates more particularly, in various embodiments, to chromatographic materials for normal phase chromatography, supercritical fluid chromatography, carbon dioxide based chromatography, hydrophobic interaction liquid chromatography, hydrophilic interaction liquid chromatography, subcritical fluid chromatography, high pressure liquid chromatography, and solvated gas chromatography that mitigate or avoid retention drift or change while exhibiting useful overall retention, as well as corresponding apparatuses, kits, methods of manufacture, and methods of use.

BACKGROUND OF THE INVENTION

Packing materials for fluid or liquid chromatography can be generally classified into two types: organic materials (e.g., polydivinylbenzene) and inorganic materials (e.g., silica). Many organic materials are chemically stable against strongly alkaline and strongly acidic mobile phases, allowing flexibility in the choice of mobile phase composition and pH. However, organic chromatographic materials can result in columns with low efficiency, particularly with low molecular-weight analytes. Many organic chromatographic materials not only lack the mechanical strength of typical chromatographic silica and also shrink and swell when the composition of the mobile phase is changed.

Silica is widely used in High Performance Liquid Chromatography (HPLC), Ultra High Performance Liquid Chromatography (UHPLC), and Supercritical Fluid Chromatography (SFC). Some applications employ silica that has been surface-derivatized with an organic functional group such as octadecyl (C18), octyl (C8), phenyl, amino, cyano, and the like. As stationary phases for HPLC, these packing materials can result in columns that have high efficiency and do not show evidence of shrinking or swelling.

Hybrid materials can provide solutions to certain chromatographic problems experienced with silica based packing materials. Hybrid materials can provide improvements including improved high and low pH stability, mechanical stability, peak shape when used at pH 7, efficiency, retentivity, and desirable chromatographic selectivity.

However, potential problems can exist for conventional hybrid materials and silica materials in other applications. One problem is poor peak shape for bases when used at low pH, which can negatively impact loadability and peak capacity when used at low pH. Another problem is a change in acidic and basic analyte retention times (denoted 'drift') after a column is exposed to repeated changes in mobile phase pH (e.g., switching repeatedly from pH 10 to 3).

Another problem is retention drift or change, for example in chromatography modes with little water (e.g., less than 5%, less than 1%). For example, retention drift or change is observed under standard SFC conditions for both silica and organic-inorganic hybrid (e.g., BEH Technology™ materials available from Waters Technologies Corporation, Milford Mass.) based chromatographic phases, bonded and unbonded. Other SFC stationary phases can also exhibit similar retention drift or change.

SUMMARY OF THE INVENTION

In various aspects and embodiments, the invention provides chromatographic materials for normal phase chromatography, supercritical fluid chromatography, carbon dioxide based chromatography, hydrophobic interaction liquid chromatography, hydrophilic interaction liquid chromatography, subcritical fluid chromatography, high pressure liquid chromatography, and solvated gas chromatography that mitigate or avoid retention drift or change while exhibiting useful overall retention, as well as corresponding apparatuses, kits, methods of manufacture, and methods of use.

The invention advantageously mitigates or avoids retention drift or change while exhibiting useful overall retention. For example, in SFC, retention drift or change can be (among various other theories) attributed to alkoxylation of solvent accessible silanols on the particle under the standard $CO_2$/MeOH mobile phase (and/or by other alcohol co-solvents) utilized for SFC. This is a problem, as users observe a change in the chromatography (e.g., retention time) obtained on their SFC system as the column ages, and again when a new, non-alkoxylated column is put on the system.

In various aspects and embodiments, the invention provides various solutions to such retention drift or change and related problems (e.g., retention, peak shape, and the like) through selection and/or modification of the chromatographic material. For example, the invention includes specialized functionalization of a chromatographic core surface (e.g., with particular functional groups, and combinations thereof), which essentially prevent chromatographic interaction between and analyte and the chromatographic core surface, which maintaining desired interaction between the analyte and the chromatographic material.

In other various aspects and embodiment, the invention relates to utilizing a chemistry which imparts a high density reactive surface modifying group to a surface of silica, polymeric or hybrid materials (including but not limited to particles, monoliths, spherical, non-spherical, granular, fully porous, and superficially porous). After coupling with selectivity inducing ligand and hydrolysis of unreacted surface modifying groups, a multi-component surface is achieved. Products of this invention have greatly reduced secondary interactions with the base particle surface (e.g., unwanted interactions, non-specific adsorption). Secondary interactions of analyte with the material surface can occur due to silanols, pendant hydrophobic groups and polymer or hybrid backbone chains. The initial coating may be used itself as a chromatographic phase, either by neutralizing the reactive moiety (i.e., hydrolysis) or without further modification (i.e., an amine or carboxylate phase) or the surface may be further modified by covalent attachment of one or more selectivity inducing ligands.

In various aspects and embodiments, the invention provides numerous advantages. For example, the invention can provide for a single solid phase capable of resolving analytes across all classes (e.g., acidic, basic and neutral) with superior retention, peak capacity and peak shape. In various example, the invention can effectively masks silanols from the analytes of interest producing a predictable and stable chromatographic separation. In various examples, the invention can effectively eliminate retention drift or change due to unwanted support surface interactions with analyte. The invention can be especially effective at masking silanols on silica or silica hybrid materials. In various examples, the invention can improve peak capacity and tailing across all analyte classes, but especially with bases. In various examples, the invention can avoid pore clogging, despite bonding with oligomeric siloxanes (e.g., as compared to conventional polymeric coatings of porous silica materials, which can result in clogging of the pores greatly decreasing the available surface area of the materials and leading to inhomogeneous surfaces—despite the promotion of oligomerization of silanes in the present invention there is no evidence of pore clogging or decreased surface area).

The invention includes various additional advantages, including but not limited to, the ability to selection/design selectivity through selection/design of the chemical modifications.

In one aspect, the present invention provides a chromatographic stationary phase material for normal phase chromatography, high-pressure liquid chromatography, solvated gas chromatography, supercritical fluid chromatography, subcritical fluid chromatography, carbon dioxide based chromatography, hydrophilic interaction liquid chromatography or hydrophobic interaction liquid chromatography represented by Formula 1: $[X](W)_a(Q)_b(T)_c$ (Formula 1). X can be a high purity chromatographic core composition having a surface including a silica core material, metal oxide core material, an inorganic-organic hybrid material or a group of block copolymers thereof. W can be absent and/or can include hydrogen and/or can include a hydroxyl on the surface of X. Q can be a functional group that minimizes retention variation over time (drift) under chromatographic conditions utilizing low water concentrations. T can include one or more hydrophilic, polar, ionizable, and/or charged functional groups that chromatographically interact with the analyte. Additionally, b and c can be positive numbers, with the ratio $0.05 \leq (b/c) \leq 100$, and $a \geq 0$.

In another aspect, the present invention provides a chromatographic stationary phase material represented by Formula 1: $[X](W)_a(Q)_b(T)_c$ (Formula 1). X can be a chromatographic core material including a silica based, metal oxide based, or inorganic-organic hybrid based core surface. W can be absent and/or can include hydrogen and/or can include hydroxyl on the surface of X. Q can include one or more functional groups that essentially prevent chromatographic interaction between an analyte, and X and W, such that a first fraction of Q is bound to X and a section fraction of Q is polymerized. T can include one or more hydrophilic, polar, ionizable, and/or charged functional groups that chromatographically interact with the analyte, such that a third fraction of T is bound to Q, a fourth fraction of T is bound to X, and a fourth fraction of T is polymerized. Additionally, b and c can be positive numbers, with the ratio $0.05 \leq (b/c) \leq 100$, and $a \geq 0$.

In one or more embodiments, Q is represented by:

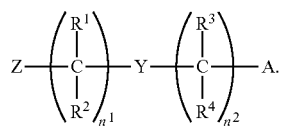

In one or more embodiments, $n^1$ is an integer from 0-30 and $n^2$ is an integer from 0-30. Each occurrence of $R^1$, $R^2$, $R^3$ and $R^4$ can independently represent hydrogen, fluoro, methyl, ethyl, n-butyl, t-butyl, i-propyl, lower alkyl, a protected or deprotected alcohol, a zwitterion, or a group Z. In some embodiments, group Z includes a surface attachment group having the formula $(B^1)_x(R^5)_y(R^6)_zSi—$, wherein x is an integer from 1-3, y is an integer from 0-2, z is an integer from 0-2, and $x+y+z=3$. Each occurrence of $R^5$ and $R^6$ can independently represent methyl, ethyl, n-butyl, iso-butyl, tert-butyl, iso-propyl, thexyl, substituted or unsubstituted aryl, cyclic alkyl, branched alkyl, lower alkyl, a protected or deprotected alcohol, or a zwitterion group and $B^1$ can represent a siloxane bond. In some embodiments, group Z includes an attachment to a surface organofunctional hybrid group through a direct carbon-carbon bond formation or through a heteroatom, ester, ether, thioether, amine, amide, imide, urea, carbonate, carbamate, heterocycle, triazole, or urethane linkage. In some embodiments, group Z includes an adsorbed, surface group that is not covalently attached to the surface of the material. Y can be an embedded polar functionality. In some embodiments, A represents a hydrophilic terminal group. In some embodiments, A represents hydrogen, fluoro, methyl, ethyl, n-butyl, t-butyl, i-propyl, lower alkyl, or group Z. In some embodiments, A represents a functionalizable group.

In one or more embodiments, T is represented by one of:

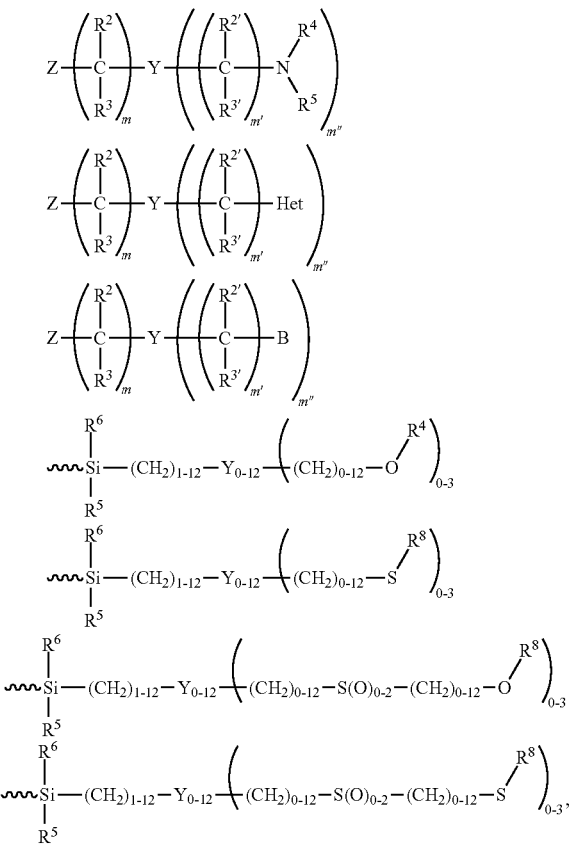

or a combination thereof. In some embodiments, m is an integer from 0-30; m' is an integer from 0-30; and m" is an integer from 0-3. In some embodiments, Z represents a surface attachment group having the formula $(B^1)_x(R^5)_y(R^6)_zSi—$, wherein x is an integer from 1-3, y is an integer from 0-2, z is an integer from 0-2, and $x+y+z=3$. Each occurrence of $R^5$ and $R^6$ can independently represent methyl, ethyl, n-butyl, iso-butyl, tert-butyl, iso-propyl, thexyl, substituted or unsubstituted aryl, cyclic alkyl, branched alkyl, lower alkyl, a protected or deprotected alcohol, or a zwitterion group. $B^1$ can represent a siloxane bond; where each of $R^{7'}$ $R^{7'}$ and $R^{7''}$ represents hydrogen, methyl, ethyl, n-butyl, iso-butyl, tert-butyl, iso-propyl, thexyl, phenyl, branched alkyl or lower alkyl. In some embodiments, Z represents an attachment to a surface organofunctional hybrid group through a direct carbon-carbon bond formation or through a heteroatom, ester, ether, thioether, amine, amide, imide, urea, carbonate, carbamate, heterocycle, triazole, or urethane linkage. In some embodiments, Z represents an adsorbed, surface group that is not covalently attached to the surface of the material.

In some embodiments, b and c are positive numbers, with a ratio $0.05 \leq (b/c) \leq 100$, and $a \geq 0$. In some embodiments, Q and T are different, whereas in other embodiments Q and T are the same. Q can include two or more different moieties, and T can include two or more different moieties. In some embodiments, the first, second, third, fourth, and fifth fraction are each independently about 0-100, 1-99, 5-95, 10-90, 20-80, 30-70, 40-60, 0, 5, 10, 15, 20, 25, 30, 35, 40, 45, 50, 55, 60, 65, 70, 75, 80, 85, 90, or 95%.

In one or more embodiments, Q is non-polar. In some embodiments, Q comprises a borate or nitro functional group. In some embodiments, Q is represented by one of:

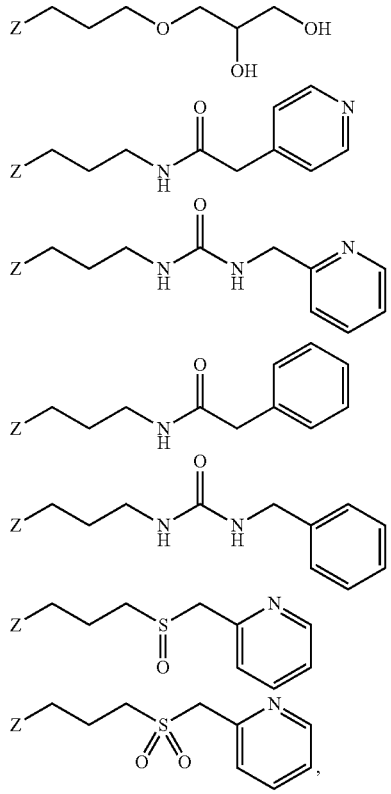

wherein Z can include a surface attachment group having the formula $(B^1)_x(R^5)_y(R^6)_z Si-$, wherein x is an integer from 1-3, y is an integer from 0-2, z is an integer from 0-2, and x+y+z=3. Each occurrence of $R^5$ and $R^6$ can independently represent methyl, ethyl, n-butyl, iso-butyl, tert-butyl, iso-propyl, thexyl, substituted or unsubstituted aryl, cyclic alkyl, branched alkyl, lower alkyl, a protected or deprotected alcohol, or a zwitterion group, and $B^1$ can represent a siloxane bond.

In another embodiment, Z is an attachment to a surface organofunctional hybrid group through a direct carbon-carbon bond formation or through a heteroatom, ester, ether, thioether, amine, amide, imide, urea, carbonate, carbamate, heterocycle, triazole, or urethane linkage. In yet another embodiment, Z is an adsorbed, surface group that is not covalently attached to the surface of the material.

In some embodiments, T is represented by one of:

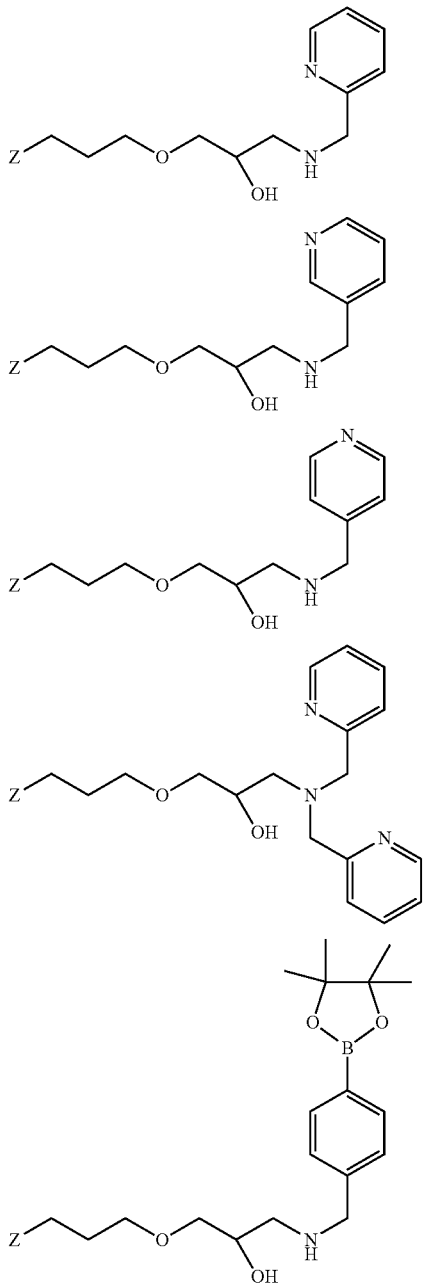

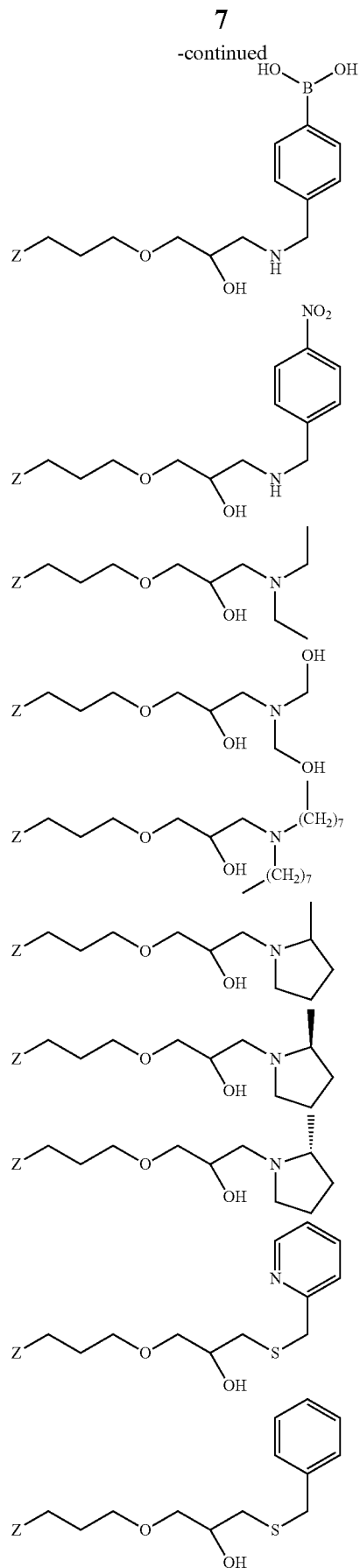
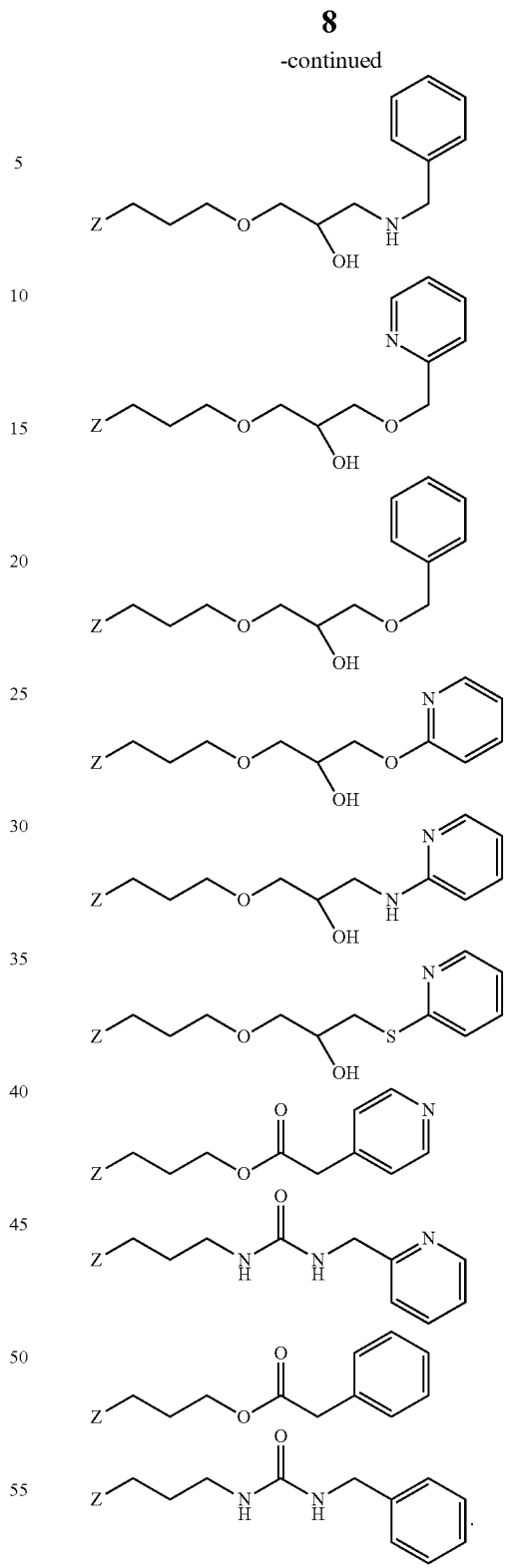

In some embodiments, Z includes a surface attachment group having the formula $(B^1)_x(R^5)_y(R^6)_z Si—$, wherein x is an integer from 1-3, y is an integer from 0-2, z is an integer from 0-2, and x+y+z=3. Each occurrence of $R^5$ and $R^6$ can independently represent methyl, ethyl, n-butyl, iso-butyl, tert-butyl, iso-propyl, thexyl, substituted or unsubstituted aryl, cyclic alkyl, branched alkyl, lower alkyl, a protected or deprotected alcohol, or a zwitterion group, and $B^1$ can represent a siloxane bond. In some embodiments, Z is an attachment to a surface organofunctional hybrid group through a direct carbon-carbon bond formation or through a heteroatom, ester, ether, thioether, amine, amide, imide, urea, carbonate, carbamate, heterocycle, triazole, or urethane linkage. In some embodiments, Z is an adsorbed, surface group that is not covalently attached to the surface of the material.

In one or more embodiments of any of the above aspects, X is a high purity chromatographic material having a core surface that is subject to alkoxylation by a chromatographic mobile phase under chromatographic conditions. X can be a chromatographic material having a core surface that is subject to alkoxylation by a chromatographic mobile phase under chromatographic conditions. In some embodiments, the functional group including Q is a diol. The functional group including T can be an amine, an ether, a thioether, or a combination thereof. T can include a chiral functional group adapted for a chiral separation, Q can include a chiral functional group adapted for a chiral separation, or T and Q can both include a chiral functional group adapted for a chiral separation.

In one or more embodiments of the above aspects, the ratio b/c is about 0.05-75, 0.05-50, 0.1, 0.2, 0.3, 0.4, 0.5, 0.6, 0.7, 0.8, 0.9, 1, 5, 10, 15, 20, 25, 30, 35, 40, 45, 50, 60, 70, 80, or 90. In some embodiments, the surface of X does not include silica, and b=0 or c=0. In some embodiments, the combined surface coverage is greater than about 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.4, 3.5, 3.6, 3.7, 3.8, 3.9, 4, 5, 6, 7, or 8 $\mu mol/m^2$.

In some embodiments of the above aspects, the chromatographic stationary phase exhibits a retention drift or change of ≤5% over 30 days, ≤4% over 30 days, ≤3% over 30 days, ≤2% over 30 days, ≤1% over 30 days, ≤5% over 10 days, ≤4% over 10 days, ≤3% over 10 days, ≤2% over 10 days, ≤1% over 10 days, ≤5% over 3 days, ≤4% over 3 days, ≤3% over 3 days, ≤2% over 3 days, ≤1% over 3 days, ≤5% over 30 runs, ≤4% over 30 runs, ≤3% over 30 runs, ≤2% over 30 runs, ≤1% over 30 runs, ≤5% over 10 runs, ≤4% over 10 runs, ≤3% over 10 runs, ≤2% over 10 runs, ≤1% over 10 runs, ≤5% over 3 runs, ≤4% over 3 runs, ≤3% over 3 runs, ≤2% over 3 runs, or ≤1% over 3 runs.

In some embodiments, the core material consists essentially of a silica material. Optionally, the core material consists essentially of an organic-inorganic hybrid material or a superficially porous material. In one or more embodiments, the core material consists essentially of an inorganic material with a hybrid surface layer, a hybrid material with an inorganic surface layer, a surrounded hybrid layer, or a hybrid material with a different hybrid surface layer. The stationary phase material can optionally be in the form of a plurality of particles, a monolith, or a superficially porous material. In some embodiments the stationary phase material does not have chromatographically enhancing pore geometry whereas in other embodiments the stationary phase material has chromatographically enhancing pore geometry. The stationary phase material can be in the form of a spherical material, non-spherical material (e.g., including toroids, polyhedron). In certain embodiments, the stationary phase material has a highly spherical core morphology, a rod shaped core morphology, a bent-rod shaped core morphology, a toroid shaped core morphology; or a dumbbell shaped core morphology. In certain embodiments, the stationary phase material has a mixture of highly spherical, rod shaped, bent rod shaped, toroid shaped, or dumbbell shaped morphologies.

In some embodiments, the stationary phase material has a surface area of about 25 to 1100 $m^2/g$, about 150 to 750 $m^2/g$, or about 300 to 500 $m^2/g$. In some embodiments, the stationary phase material has a pore volume of about 0.2 to 2.0 $cm^3/g$, or about 0.7 to 1.5 $cm^3/g$. In some embodiments, the stationary phase material has a micropore surface area of less than about 105 $m^2/g$, less than about 80 $m^2/g$, or less than about 50 $m^2/g$. The stationary phase material can have an average pore diameter of about 20 to 1500 Å, about 50 to 1000 Å, about 60 to 750 Å, or about 65 to 200 Å. In some embodiments, the plurality of particles have sizes between about 0.2 and 100 microns, between about 0.5 and 10 microns, or between about 1.5 and 5 microns.

In one or more embodiments, X includes a silica core, c=0, and Q has a combined surface coverage of ≥2.5, 2.6, 2.7, 2.8, 2.9, 3.0, 3.5, 4.0, 4.5, or 5 $\mu mol/m^2$; or X includes a non-silica core or a silica-organic hybrid core, c=0, and Q has a combined surface coverage of ≥0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5, or 5 $\mu mol/m^2$; or b>0, c>0, and Q has a combined surface coverage of ≥0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5, or 5 $\mu mol/m^2$.

The chromatographic stationary phase can be adapted for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography.

In yet another aspect, the present invention provides a chromatographic stationary phase material represented by Formula 1: $[X](W)_a(Q)_b(T)_c$ (Formula 1). X can be a chromatographic core material that is subject to retention drift or change under normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography conditions. W can be absent and/or can include hydrogen and/or can include hydroxyl on the surface of X. Q can include functional groups that essentially prevent chromatographic interaction between an analyte, and X and W. T can include functional groups that chromatographically interact with the analyte, and is bound to X through Q. "b" and "c: can be positive numbers, such that 0.05≤(b/c)≤100, and a≥0.

In some embodiments, the chromatographic stationary phase material is adapted for normal phase chromatography, supercritical fluid chromatography, subcritical fluid chromatography, carbon dioxide based chromatography, hydrophobic interaction liquid chromatography, high pressure liquid chromatography, solvated gas chromatography, or a combination thereof.

In some embodiments, the chromatographic stationary phase includes radially adjusted pores, non-radially adjusted pores, ordered pores, non-ordered pores, monodispersed pores, non-monodispersed pores, smooth surfaces, rough surfaces or combinations thereof. In one or more embodiments, T has one ionizable group, T has more than one ionizable group, T has two or more ionizable groups of the same pKa, or T has two or more ionizable group of different pKa.

In yet another aspect, the present invention provides a column, capillary column, microfluidic device or apparatus for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography. The column, capillary column, microfluidic device or apparatus includes a housing having at least one wall defining a chamber having an entrance and an exit, and a stationary phase including any of the chromatographic materials of the present disclosure disposed therein. The housing and stationary phase can be adapted for normal phase chromatography, supercritical fluid chromatography, carbon dioxide based chromatography, or hydrophobic interaction liquid chromatography.

In yet another aspect, the present invention provides a kit for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography. The kit can include a housing having at least one wall defining a chamber having an entrance and an exit, and a stationary phase according to any of the materials of the present invention disposed therein. The housing and stationary phase can be adapted for normal phase chromatography, supercritical fluid chromatography, carbon dioxide based chromatography, or hydrophobic interaction liquid chromatography. The kit can further include instructions for performing normal phase chromatography, supercritical fluid chromatography, carbon dioxide based chromatography, or hydrophobic interaction liquid chromatography with the housing and stationary phase.

In yet another aspect, the present disclosure provides a method for preparing a stationary phase including any of the materials of the present disclosure. The method includes reacting a core surface with a silane coupling agent having a pendant reactive group. The method further includes reacting a second chemical agent including one or more hydrophilic, polar, ionizable, and/or charged functional groups with the pendant reactive group. The method further includes neutralizing any remaining unreacted pendant reactive groups, thereby producing a stationary phase according to the present disclosure.

In yet another aspect, the present disclosure provides a method for preparing a stationary phase according to any of the materials of the present disclosure. The method includes oligomerizing a silane coupling agent having a pendant reactive group. The method further includes reacting a core surface with the oligomerized silane coupling agent. The method further includes reacting a second chemical agent including one or more hydrophilic, polar, ionizable, and/or charged functional groups with the pendant reactive group. The method further includes neutralizing any remaining unreacted pendant reactive groups, thereby producing a stationary phase according to the present disclosure.

In one or more embodiments, Q is derived from a reagent having one or the following structures:

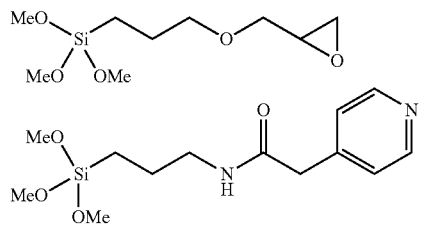

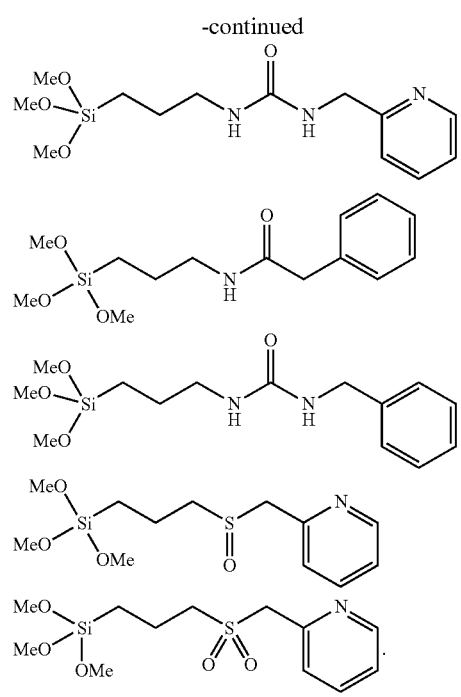

In some embodiments, T is derived from a reagent having one or the following structures:

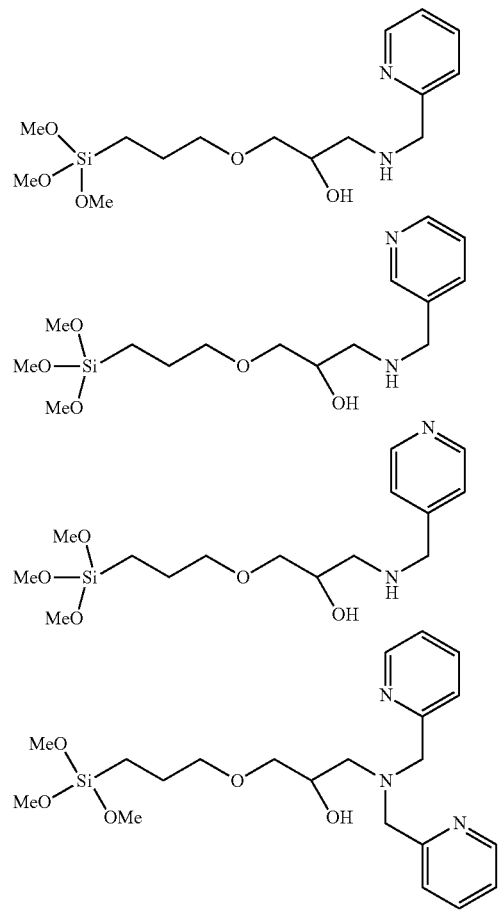

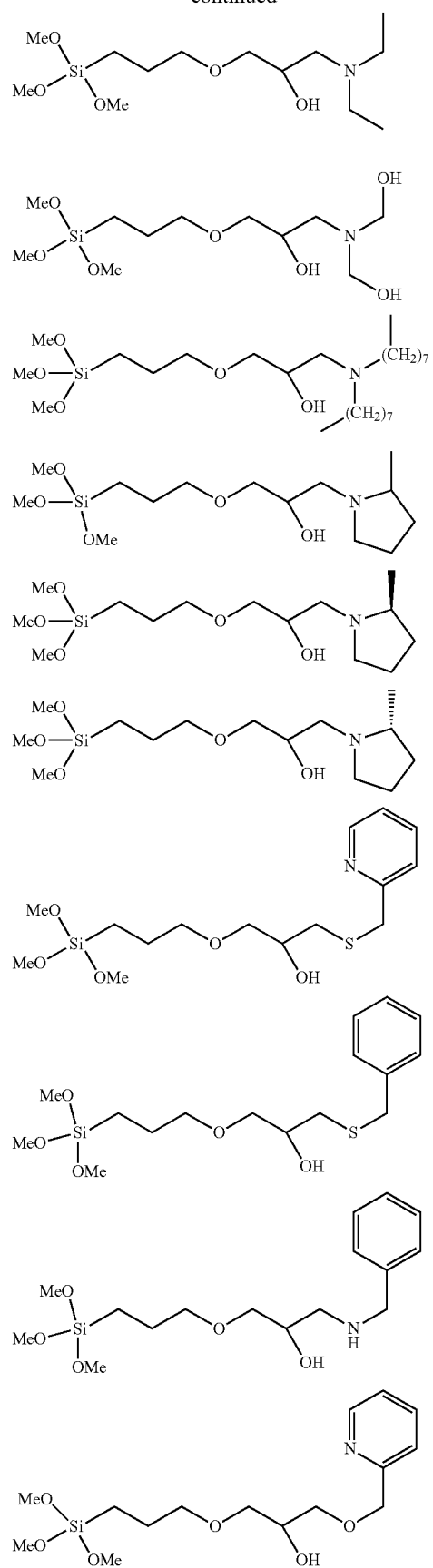
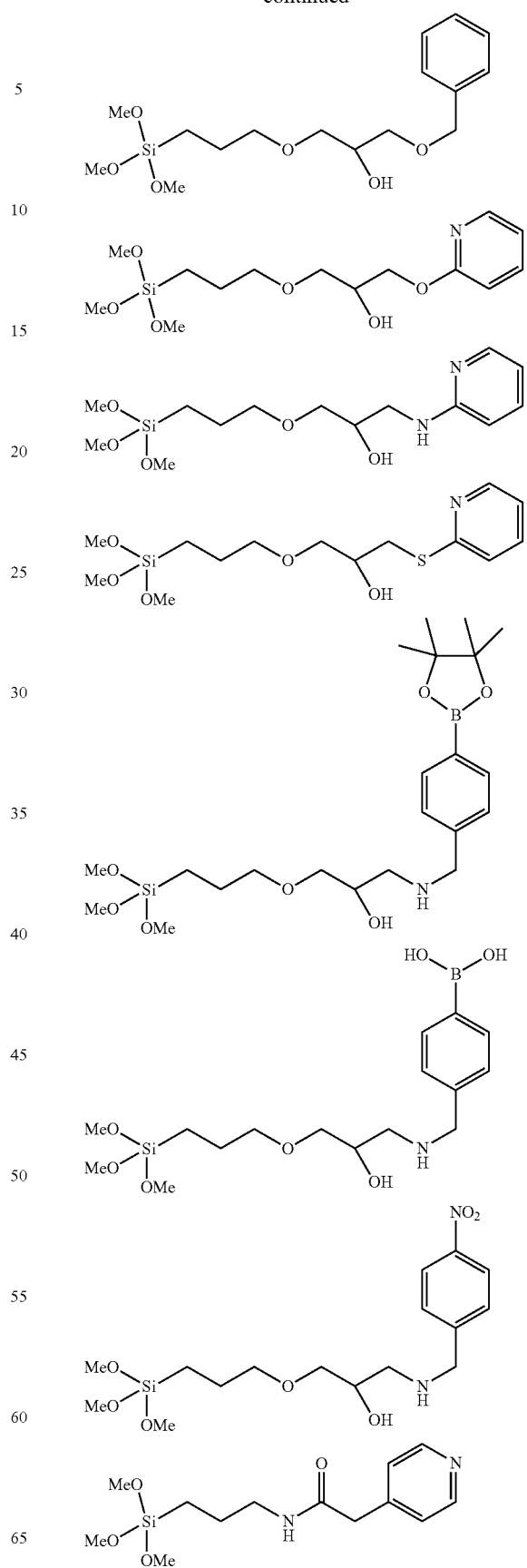

-continued

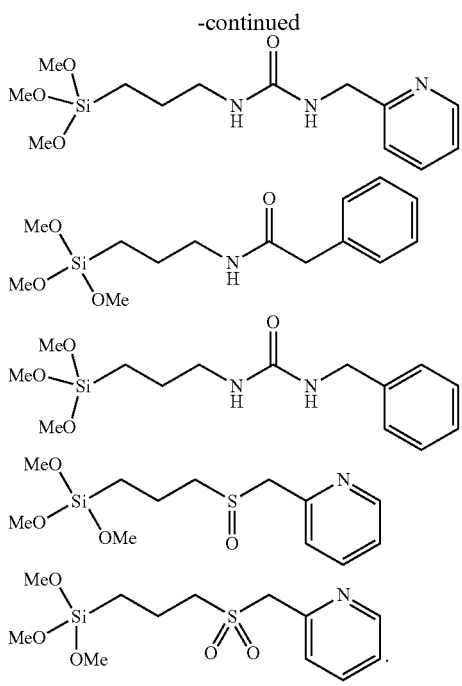

In yet another aspect, the invention provides a method for mitigating or preventing retention drift or change in normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography. The invention includes chromatographically separating a sample using a chromatographic device including a chromatographic stationary phase according to the present disclosure, thereby mitigating or preventing retention drift or change.

In one or more embodiments, mitigating or preventing retention drift or change includes a retention drift or change of ≤5% over 30 days, ≤4% over 30 days, ≤3% over 30 days, ≤2% over 30 days, ≤1% over 30 days, ≤5% over 10 days, ≤4% over 10 days, ≤3% over 10 days, ≤2% over 10 days, ≤1% over 10 days, ≤5% over 3 days, ≤4% over 3 days, ≤3% over 3 days, ≤2% over 3 days, ≤1% over 3 days, ≤5% over 30 runs, ≤4% over 30 runs, ≤3% over 30 runs, ≤2% over 30 runs, ≤1% over 30 runs, ≤5% over 10 runs, ≤4% over 10 runs, ≤3% over 10 runs, ≤2% over 10 runs, ≤1% over 10 runs, ≤5% over 3 runs, ≤4% over 3 runs, ≤3% over 3 runs, ≤2% over 3 runs, or ≤1% over 3 runs. In some embodiments, mitigating or preventing retention drift or change includes substantially eliminating the effect of alkoxylation and/or dealkoxylation of the chromatographic material on retention.

In some embodiments, T includes one of the following structures:

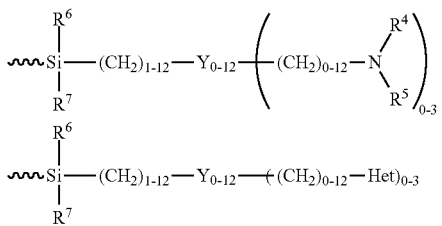

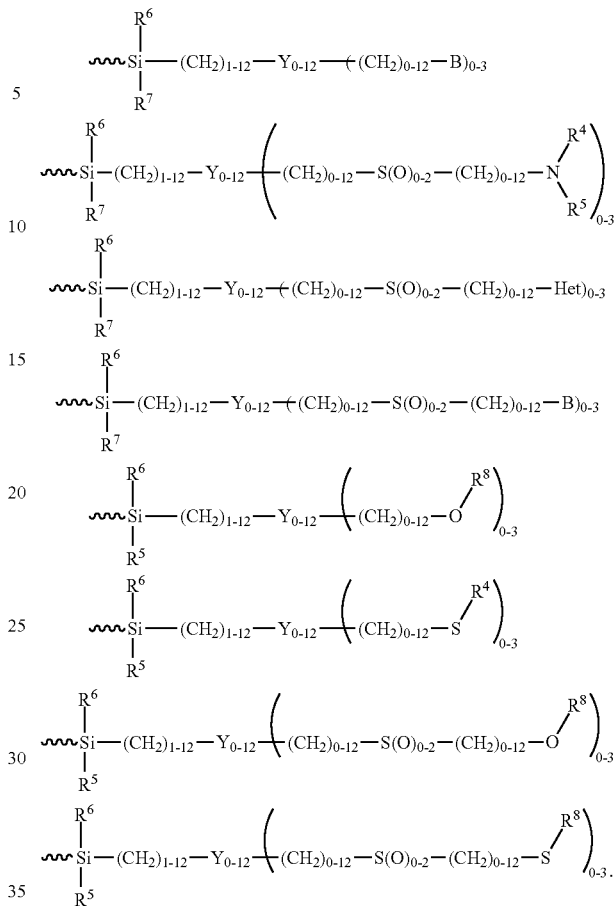

In some embodiments, Y includes one of the following structures:

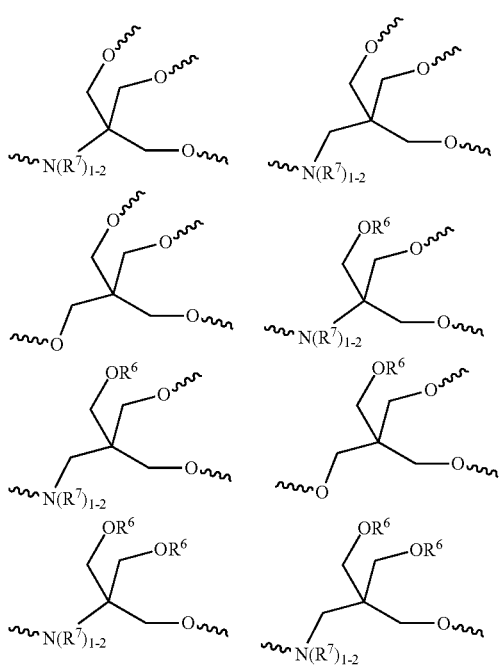

-continued
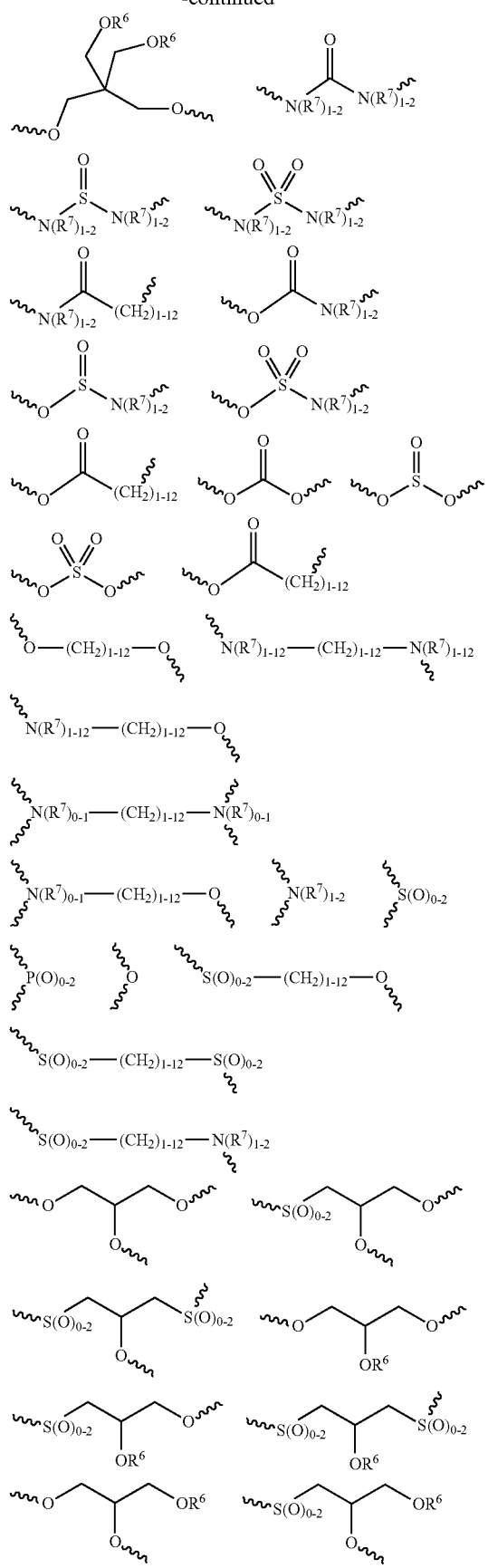
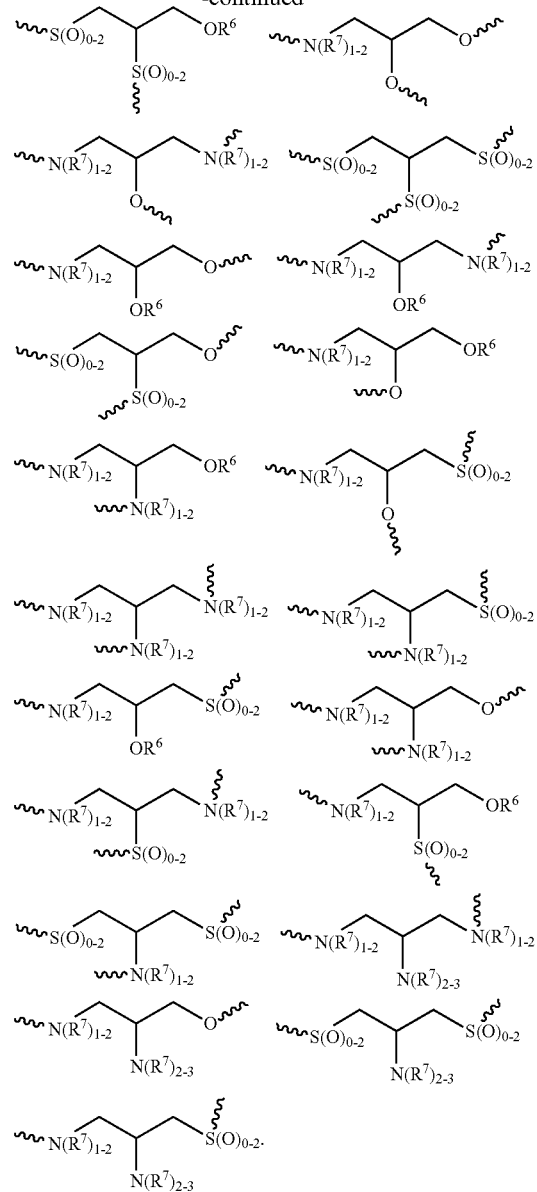
T can be derived from a reagent represented by:
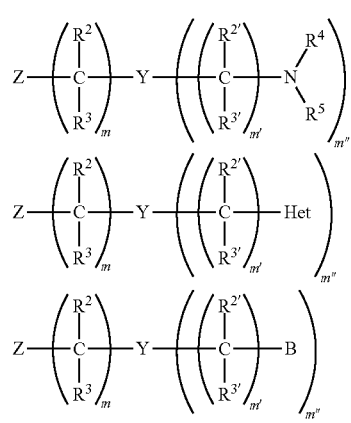

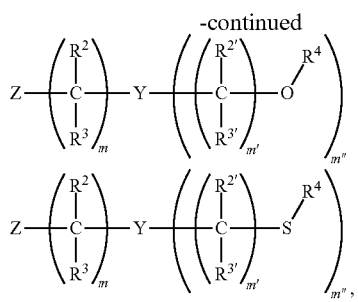

or a combination thereof, wherein m is an integer from 0-30; m' is an integer from 0-30; and m" is an integer from 0-3. Z can represent a chemically reactive group including:

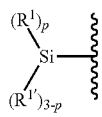

—OH, —OR$^6$, amine, alkylamine, dialkylamine, isocyanate, acyl chloride, triflate, isocyanate, thiocyanate, imidazole carbonate, NHS-ester, carboxylic acid, ester, epoxide, alkyne, alkene, azide, —Br, —Cl, or —I. Y can be an embedded polar functionality. Each occurrence of R$^1$ can independently represent a chemically reactive group on silicon, including (but not limited to) —H, —OH, —OR$^6$, dialkylamine, triflate, Br, Cl, I, vinyl, alkene, or —(CH$_2$)$_m$Q; Each occurrence of Q can be —OH, —OR$^6$, amine, alkylamine, dialkylamine, isocyanate, acyl chloride, triflate, isocyanate, thiocyanate, imidazole carbonate, NHS-ester, carboxylic acid, ester, epoxide, alkyne, alkene, azide, —Br, —Cl, or —I. p can be an integer from 1-3. Each occurrence of R$^{1'}$ can independently represent F, C$_1$-C$_{18}$ alkyl, C$_2$-C$_{18}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, C$_5$-C$_{18}$ aryloxy, or C$_1$-C$_{18}$ heteroaryl, fluoroalkyl, or fluoroaryl. Each occurrence of R$^2$ and R$^3$ can independently represent hydrogen, C$_1$-C$_{18}$ alkyl, C$_2$-C$_{18}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, C$_5$-C$_{18}$ aryloxy, or C$_1$-C$_{18}$ heteroaryl, —Z, or a group having the formula —Si(R')$_b$R"$_a$ or —C(R')$_b$R"$_a$. The variables a and b can each represent an integer from 0 to 3, provided that a+b=3. R' can represent a C$_1$-C$_6$ straight, cyclic or branched alkyl group. R" can be a functionalizing group selected from the group consisting of alkyl, alkenyl, alkynyl, aryl, cyano, amino, diol, nitro, ester, a cation or anion exchange group, an alkyl or aryl group containing an embedded polar functionality and a chiral moiety. R$^4$ can represent hydrogen, C$_1$-C$_{18}$ alkyl, C$_2$-C$_{18}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, substituted aryl, C$_5$-C$_{18}$ aryloxy, or C$_1$-C$_{18}$ heteroaryl. R$^5$ can represent hydrogen, C$_1$-C$_{15}$ alkyl, C$_2$-C$_{15}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, substituted aryl, C$_5$-C$_{18}$ aryloxy, or C$_1$-C$_{18}$ heteroaryl. Each occurrence of R$^6$ can independently represent C$_1$-C$_{18}$ alkyl, C$_2$-C$_{18}$ alkenyl, C$_2$-C$_{18}$ alkynyl, C$_3$-C$_{18}$ cycloalkyl, C$_1$-C$_{18}$ heterocycloalkyl, C$_5$-C$_{18}$ aryl, C$_5$-C$_{18}$ aryloxy, or C$_1$-C$_{18}$ heteroaryl. Het can represent a monocyclic or bicyclic heterocyclic or heteroaryl ring system including at least one nitrogen atom. B can represent an acidic ionizable modifier.

The present invention is described in further detail by the drawings and examples below, which are used only for illustration purposes and are not limiting.

BRIEF DESCRIPTION OF THE DRAWINGS

The present invention can be more readily understood in the context of the following drawings and Detailed Description. It will be understood by a practitioner of ordinary skill in the art that the following drawings are not necessarily to scale, emphasis instead being placed on illustrating the inventive concepts of the present invention.

FIG. 1 shows the structure of glycidoxypropyltrimethoxysilane (GPTMS) as FIG. 1A and 2-picolylamine as FIG. 1B.

DETAILED DESCRIPTION OF THE INVENTION

Figure 2:
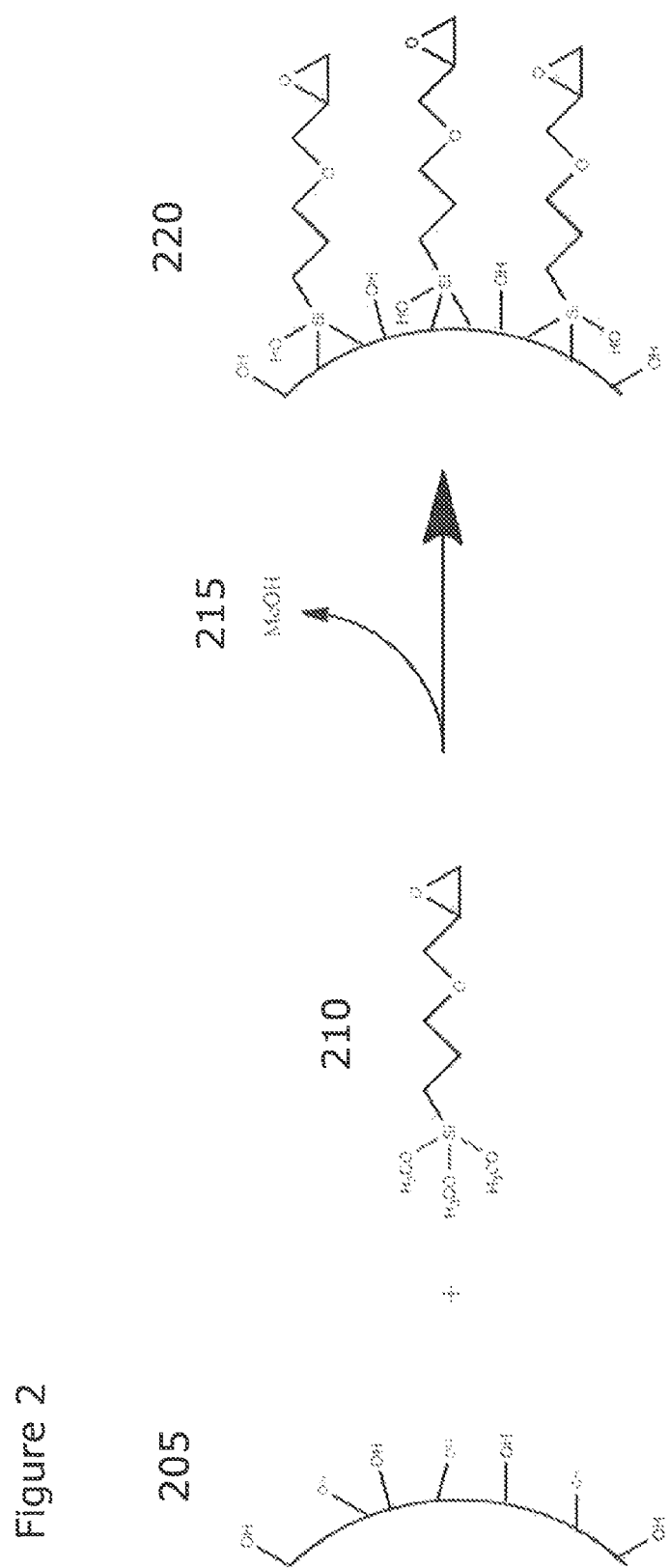
FIG. 2 shows a schematic of a reaction between an unmodified chromatographic surface and GPTMS.

In various aspects and embodiments, the invention provides chromatographic materials for normal phase chromatography, supercritical fluid chromatography, carbon dioxide based chromatography, hydrophobic interaction liquid chromatography, hydrophilic interaction liquid chromatography, subcritical fluid chromatography, high pressure liquid chromatography, and solvated gas chromatography that mitigate or avoid retention drift or change while exhibiting useful overall retention, as well as corresponding apparatuses, kits, methods of manufacture, and methods of use.

The invention advantageously mitigates or avoids retention drift or change while exhibiting useful overall retention. For example, in SFC, retention drift or change can be (among various other theories) attributed to alkoxylation of solvent accessible silanols on the particle under the standard CO$_2$/MeOH mobile phase (and/or by other alcohol co-solvents) utilized for SFC. This is a problem, as users observe a change in the chromatography (e.g., retention time) obtained on their SFC system as the column ages, and again when a new, non-alkoxylated column is put on the system.

In various aspects and embodiments, the invention provides various solutions to such retention drift or change and related problems (e.g., retention, peak shape, and the like) through selective modification of chromatographic materials.

Definitions

In various aspects and embodiments, the invention provides for mitigating or preventing retention drift or change. "Retention drift" or "retention change" can include an undesired difference in elution time between chromatographic runs or experiments (e.g., in run 1, peak x elutes at time y, but in run 1+n, peak x elutes at time z). Thus, retention drift or change can result in undesired effects including experimental noise, irreproducibility, or failure. Accordingly, in a broad sense, mitigating or preventing retention drift or change includes addressing or counteracting an undesired difference in elution times between chromatographic runs, to the extent that the chromatographic experiment provides and chromatographically acceptable result.

In some embodiments, mitigating or preventing retention drift or change is not constant an absolute or constant value. For example, the amount of retention drift or change the can occur while still achieving a chromatographically acceptable result can vary depending upon the acceptable error or variance in a given experiment, the complexity of a sample (e.g., number and/or separation of peaks). The amount of retention drift or change the can occur while still achieving a chromatographically acceptable result can vary depending upon the duration or required reproducibility a given experiment (e.g., if reproducibility is required over a greater number of runs, the allowable retention drift or change between runs can be smaller). Therefore, it should be clear that mitigating or preventing retention drift or change does not necessarily mean the absolute elimination of retention drift or change.

In some embodiments, mitigating or preventing retention drift or change can be quantified. For example, retention drift or change can be measured for a single peak, or averaged over a set of peaks. Retention drift or change can be measured over a given period of time or number of runs. Retention drift or change can be measured relative to a standard value, starting value, or between two or more given runs.

Furthermore, retention drift or change can be quantified by a standardized test. In the examples discussed below, the following standardized test was employed: The Average % Retention Change was calculated by taking the percent difference of the average absolute peak retentions measured from the day 3, 10 or 30 chromatographic tests from the average absolute peak retentions measured on the day one chromatographic test. For each day tested, the columns were equilibrated under Mix1 test conditions for 20 minutes followed by three injections of Mix1 and then equilibrated under Mix2 Test conditions for 10 minutes, followed by three injections of Mix2.

The parameters for this standardized test are: Co-Solvent Mix1=5% methanol; Sample Mix1=3-benzoylpyridine (0.1 mg/mL); Co-Solvent Mix2=10% methanol; Sample Mix2=caffeine, thymine, papaverine, prednisolone, sulfanilamide (0.2 mg/mL each); Column Dimension=2.1×150 mm; Flow Rate=1.0 mL/min; Column Temperature=50° C.; Back Pressure=1800 psi; Detector=Waters Technologies Corporation ACQUITY® PDA with SFC Flow Cell; Detector Setting=254 nm 40 spec/sec; Weak Needle Wash=iso-propanol; and Injection=1.0 μL (2.0 μL loop with PLUNO injection mode).

In accordance with this standardized test, mitigating or preventing retention drift or change can comprises a retention drift or change of ≤5% over 30 days, ≤4% over 30 days, ≤3% over 30 days, ≤2% over 30 days, ≤1% over 30 days, ≤5% over 10 days, ≤4% over 10 days, ≤3% over 10 days, ≤2% over 10 days, ≤1% over 10 days, ≤5% over 3 days, ≤4% over 3 days, ≤3% over 3 days, ≤2% over 3 days, ≤1% over 3 days, ≤5% over 30 runs, ≤4% over 30 runs, ≤3% over 30 runs, ≤2% over 30 runs, ≤1% over 30 runs, ≤5% over 10 runs, ≤4% over 10 runs, ≤3% over 10 runs, ≤2% over 10 runs, ≤1% over 10 runs, ≤5% over 3 runs, ≤4% over 3 runs, ≤3% over 3 runs, ≤2% over 3 runs, or ≤1% over 3 runs.

In other embodiments, mitigating or preventing retention drift or change can comprises a retention drift or change of ≤5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1% over 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 days (or runs).

"High Purity" or "high purity chromatographic material" includes a material which is prepared form high purity precursors. In certain aspects, high purity materials have reduced metal contamination and/or non-diminished chromatographic properties including, but not limited to, the acidity of surface silanols and the heterogeneity of the surface.

"Chromatographic surface" includes a surface which provides for chromatographic separation of a sample. In certain aspects, the chromatographic surface is porous. In some aspects, a chromatographic surface can be the surface of a particle, a superficially porous material or a monolith. In certain aspects, the chromatographic surface is composed of the surface of one or more particles, superficially porous materials or monoliths used in combination during a chromatographic separation. In certain other aspects, the chromatographic surface is non-porous.

"Ionizable modifier" includes a functional group which bears an electron donating or electron withdrawing group. In certain aspects, the ionizable modifier contains one or more carboxylic acid groups, amino groups, imido groups, amido groups, pyridyl groups, imidazolyl groups, ureido groups, thionyl-ureido groups or aminosilane groups, or a combination thereof. In other aspects, the ionizable modifier contains a group bearing a nitrogen or phosphorous atom having a free electron lone pair. In certain aspects, the ionizable modifier is covalently attached to the material surface and has an ionizable group. In some instances it is attached to the chromatographic material by chemical modification of a surface hybrid group.

"Hydrophobic surface group" includes a surface group on the chromatographic surface which exhibits hydrophobicity. In certain aspects, a hydrophobic group can be a carbon bonded phase such as a $C_4$ to $C_{18}$ bonded phase. In other aspects, a hydrophobic surface group can contain an embedded polar group such that the external portion of the hydrophobic surface maintains hydrophobicity. In some instances it is attached to the chromatographic material by chemical modification of a surface hybrid group. In other instances the hydrophobic group can be $C_4$-$C_{30}$, embedded polar, chiral, phenylalkyl, or pentafluorophenyl bonding and coatings.

"Chromatographic core" includes chromatographic materials, including but not limited to an organic material such as silica or a hybrid material, as defined herein, in the form of a particle, a monolith or another suitable structure which forms an internal portion of the materials of the invention. In certain aspects, the surface of the chromatographic core represents the chromatographic surface, as defined herein, or represents a material encased by a chromatographic surface, as defined herein. The chromatographic surface material can be disposed on or bonded to or annealed to the chromatographic core in such a way that a discrete or distinct transition is discernible or can be bound to the chromatographic core in such a way as to blend with the surface of the chromatographic core resulting in a gradation of materials and no discrete internal core surface. In certain embodiments, the chromatographic surface material can be the same or different from the material of the chromatographic core and can exhibit different physical or physiochemical properties from the chromatographic core, including, but not limited to, pore volume, surface area, average pore diameter, carbon content or hydrolytic pH stability.

"Hybrid," including "hybrid inorganic/organic material," includes inorganic-based structures wherein an organic functionality is integral to both the internal or "skeletal" inorganic structure as well as the hybrid material surface. The inorganic portion of the hybrid material can be, e.g., alumina, silica, titanium, cerium, or zirconium or oxides thereof, or ceramic material. "Hybrid" includes inorganic-based structures wherein an organic functionality is integral to both the internal or "skeletal" inorganic structure as well as the hybrid material surface. As noted above, exemplary hybrid materials are shown in U.S. Pat. Nos. 4,017,528, 6,528,167, 6,686,035 and 7,175,913, the contents of which are incorporated herein by reference in their entirety.

The term "alicyclic group" includes closed ring structures of three or more carbon atoms. Alicyclic groups include cycloparaffins or naphthenes which are saturated cyclic hydrocarbons, cycloolefins, which are unsaturated with two or more double bonds, and cycloacetylenes which have a triple bond. They do not include aromatic groups. Examples of cycloparaffins include cyclopropane, cyclohexane and cyclopentane. Examples of cycloolefins include cyclopentadiene and cyclooctatetraene. Alicyclic groups also include fused ring structures and substituted alicyclic groups such as alkyl substituted alicyclic groups. In the instance of the alicyclics such substituents can further comprise a lower alkyl, a lower alkenyl, a lower alkoxy, a lower alkylthio, a lower alkylamino, a lower alkylcarboxyl, a nitro, a hydroxyl, —$CF_3$, —CN, or the like.

The term "aliphatic group" includes organic compounds characterized by straight or branched chains, typically having between 1 and 22 carbon atoms. Aliphatic groups include alkyl groups, alkenyl groups and alkynyl groups. In complex structures, the chains can be branched or cross-linked. Alkyl groups include saturated hydrocarbons having one or more carbon atoms, including straight-chain alkyl groups and branched-chain alkyl groups. Such hydrocarbon moieties can be substituted on one or more carbons with, for example, a halogen, a hydroxyl, a thiol, an amino, an alkoxy, an alkylcarboxy, an alkylthio, or a nitro group. Unless the number of carbons is otherwise specified, "lower aliphatic" as used herein means an aliphatic group, as defined above (e.g., lower alkyl, lower alkenyl, lower alkynyl), but having from one to six carbon atoms. Representative of such lower aliphatic groups, e.g., lower alkyl groups, are methyl, ethyl, n-propyl, isopropyl, 2-chloropropyl, n-butyl, sec-butyl, 2-aminobutyl, isobutyl, tert-butyl, 3-thiopentyl and the like. As used herein, the term "nitro" means —$NO_2$; the term "halogen" designates —F, —Cl, —Br or —I; the term "thiol" means SH; and the term "hydroxyl" means —OH. Thus, the term "alkylamino" as used herein means an alkyl group, as defined above, having an amino group attached thereto. Suitable alkylamino groups include groups having 1 to about 12 carbon atoms, preferably from 1 to about 6 carbon atoms. The term "alkylthio" refers to an alkyl group, as defined above, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group, as defined above, having a carboxyl group attached thereto. The term "alkoxy" as used herein means an alkyl group, as defined above, having an oxygen atom attached thereto. Representative alkoxy groups include groups having 1 to about 12 carbon atoms, preferably 1 to about 6 carbon atoms, e.g., methoxy, ethoxy, propoxy, tert-butoxy and the like. The terms "alkenyl" and "alkynyl" refer to unsaturated aliphatic groups analogous to alkyls, but which contain at least one double or triple bond respectively. Suitable alkenyl and alkynyl groups include groups having 2 to about 12 carbon atoms, preferably from 1 to about 6 carbon atoms.

The term "alkyl" includes saturated aliphatic groups, including straight-chain alkyl groups, branched-chain alkyl groups, cycloalkyl (alicyclic) groups, alkyl substituted cycloalkyl groups and cycloalkyl substituted alkyl groups. In certain embodiments, a straight chain or branched chain alkyl has 30 or fewer carbon atoms in its backbone, e.g., $C_1$-$C_{30}$ for straight chain or $C_3$-$C_{30}$ for branched chain. In certain embodiments, a straight chain or branched chain alkyl has 20 or fewer carbon atoms in its backbone, e.g., $C_1$-$C_{20}$ for straight chain or $C_3$-$C_2$0 for branched chain, and more preferably 18 or fewer. Likewise, preferred cycloalkyls have from 4-10 carbon atoms in their ring structure and more preferably have 4-7 carbon atoms in the ring structure. The term "lower alkyl" refers to alkyl groups having from 1 to 6 carbons in the chain and to cycloalkyls having from 3 to 6 carbons in the ring structure.

Moreover, the term "alkyl" (including "lower alkyl") as used throughout the specification and claims includes both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfate, sulfonato, sulfamoyl, sulfonamido, nitro, trifluoromethyl, cyano, azido, heterocyclyl, aralkyl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl, e.g., having 1 to 3 separate or fused rings and from 6 to about 18 carbon ring atoms, e.g., phenylmethyl(benzyl).

The term "amino," as used herein, refers to an unsubstituted or substituted moiety of the formula —$NR_aR_b$, in which $R_a$ and $R_b$ are each independently hydrogen, alkyl, aryl, or heterocyclyl, or $R_a$ and $R_b$, taken together with the nitrogen atom to which they are attached, form a cyclic moiety having from 3 to 8 atoms in the ring. Thus, the term "amino" includes cyclic amino moieties such as piperidinyl or pyrrolidinyl groups, unless otherwise stated. An "amino-substituted amino group" refers to an amino group in which at least one of $R_a$ and $R_b$, is further substituted with an amino group.

The term "aromatic group" includes unsaturated cyclic hydrocarbons containing one or more rings. Aromatic groups include 5- and 6-membered single-ring groups which can include from zero to four heteroatoms, for example, benzene, pyrrole, furan, thiophene, imidazole, oxazole, thiazole, triazole, pyrazole, pyridine, pyrazine, pyridazine and pyrimidine and the like. The aromatic ring can be substituted at one or more ring positions with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like.

The term "aryl" includes 5- and 6-membered single-ring aromatic groups that can include from zero to four heteroatoms, for example, unsubstituted or substituted benzene, pyrrole, furan, thiophene, imidazole, oxazole, thiazole, triazole, pyrazole, pyridine, pyrazine, pyridazine and pyrimidine and the like. Aryl groups also include polycyclic fused aromatic groups such as naphthyl, quinolyl, indolyl and the like. The aromatic ring can be substituted at one or more ring positions with such substituents, e.g., as described above for alkyl groups. Suitable aryl groups include unsubstituted and substituted phenyl groups. The term "aryloxy" as used herein means an aryl group, as defined above, having an oxygen atom attached thereto. The term "aralkoxy" as used herein means an aralkyl group, as defined above, having an oxygen atom attached thereto. Suitable aralkoxy groups have 1 to 3 separate or fused rings and from 6 to about 18 carbon ring atoms, e.g., O-benzyl.

The term "ceramic precursor" is intended include any compound that results in the formation of a ceramic material.

The term "chiral moiety" is intended to include any functionality that allows for chiral or stereoselective syntheses. Chiral moieties include, but are not limited to, substituent groups having at least one chiral center, natural and unnatural amino-acids, peptides and proteins, derivatized cellulose, macrocyclic antibiotics, cyclodextrins, crown ethers, and metal complexes.

The term "embedded polar functionality" is a functionality that provides an integral polar moiety such that the interaction with basic samples due to shielding of the unreacted silanol groups on the silica surface is reduced. Embedded polar functionalities include, but are not limited to carbonate, amide, urea, ether, thioether, sulfinyl, sulfoxide, sulfonyl, thiourea, thiocarbonate, thiocarbamate, ethylene glycol, heterocyclic, triazole functionalities or carbamate functionalities such as disclosed in U.S. Pat. No. 5,374,755, and chiral moieties.

The language "chromatographically-enhancing pore geometry" includes the geometry of the pore configuration of the presently-disclosed materials, which has been found to enhance the chromatographic separation ability of the material, e.g., as distinguished from other chromatographic media in the art. For example, a geometry can be formed, selected or constructed, and various properties and/or factors can be used to determine whether the chromatographic separations ability of the material has been "enhanced," e.g., as compared to a geometry known or conventionally used in the art. Examples of these factors include high separation efficiency, longer column life and high mass transfer properties (as evidenced by, e.g., reduced band spreading and good peak shape.) These properties can be measured or observed using art-recognized techniques. For example, the chromatographically-enhancing pore geometry of the present porous inorganic/organic hybrid materials is distinguished from the prior art materials by the absence of "ink bottle" or "shell shaped" pore geometry or morphology, both of which are undesirable because they, e.g., reduce mass transfer rates, leading to lower efficiencies.

Chromatographically-enhancing pore geometry is found in hybrid materials containing only a small population of micropores. A small population of micropores is achieved in hybrid materials when all pores of a diameter of about <34 Å contribute less than about 110 m$^2$/g to the specific surface area of the material. Hybrid materials with such a low micropore surface area (MSA) give chromatographic enhancements including high separation efficiency and good mass transfer properties (as evidenced by, e.g., reduced band spreading and good peak shape). Micropore surface area (MSA) is defined as the surface area in pores with diameters less than or equal to 34 Å, determined by multipoint nitrogen sorption analysis from the adsorption leg of the isotherm using the BJH method. As used herein, the acronyms "MSA" and "MPA" are used interchangeably to denote "micropore surface area."

The term "functionalizing group" includes organic functional groups which impart a certain chromatographic functionality to a chromatographic stationary phase.

The term "heterocyclic group" includes closed ring structures in which one or more of the atoms in the ring is an element other than carbon, for example, nitrogen, sulfur, or oxygen. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —CF$_3$, —CN, or the like. Suitable heteroaromatic and heteroalicyclic groups generally will have 1 to 3 separate or fused rings with 3 to about 8 members per ring and one or more N, O or S atoms, e.g., coumarinyl, quinolinyl, pyridyl, pyrazinyl, pyrimidyl, furyl, pyrrolyl, thienyl, thiazolyl, oxazolyl, imidazolyl, indolyl, benzofuranyl, benzothiazolyl, tetrahydrofuranyl, tetrahydropyranyl, piperidinyl, morpholino and pyrrolidinyl.

The term "metal oxide precursor" is intended include any compound that contains a metal and results in the formation of a metal oxide, e.g., alumina, silica, titanium oxide, zirconium oxide.

The term "monolith" is intended to include a collection of individual particles packed into a bed formation, in which the shape and morphology of the individual particles are maintained. The particles are advantageously packed using a material that binds the particles together. Any number of binding materials that are well known in the art can be used such as, for example, linear or cross-linked polymers of divinylbenzene, methacrylate, urethanes, alkenes, alkynes, amines, amides, isocyanates, or epoxy groups, as well as condensation reactions of organoalkoxysilanes, tetraalkoxysilanes, polyorganoalkoxysiloxanes, polyethoxysiloxanes, and ceramic precursors. In certain embodiments, the term "monolith" also includes hybrid monoliths made by other methods, such as hybrid monoliths detailed in U.S. Pat. No. 7,250,214; hybrid monoliths prepared from the condensation of one or more monomers that contain 0-99 mole percent silica (e.g., SiO$_2$); hybrid monoliths prepared from coalesced porous inorganic/organic particles; hybrid monoliths that have a chromatographically-enhancing pore geometry; hybrid monoliths that do not have a chromatographically-enhancing pore geometry; hybrid monoliths that have ordered pore structure; hybrid monoliths that have non-periodic pore structure; hybrid monoliths that have non-crystalline or amorphous molecular ordering; hybrid monoliths that have crystalline domains or regions; hybrid monoliths with a variety of different macropore and mesopore properties; and hybrid monoliths in a variety of different aspect ratios. In certain embodiments, the term "monolith" also includes inorganic monoliths, such as those described in G. Guiochon/*J. Chromatogr. A* 1168 (2007) 101-168.

The term "nanoparticle" is a microscopic particle/grain or microscopic member of a powder/nanopowder with at least one dimension less than about 100 nm, e.g., a diameter or particle thickness of less than about 100 nm (0.1 mm), which can be crystalline or noncrystalline. Nanoparticles have properties different from, and often superior to, those of conventional bulk materials including, for example, greater strength, hardness, ductility, sinterability, and greater reactivity among others. Considerable scientific study continues to be devoted to determining the properties of nanomaterials, small amounts of which have been synthesized (mainly as nano-size powders) by a number of processes including colloidal precipitation, mechanical grinding, and gas-phase nucleation and growth. Extensive reviews have documented recent developments in nano-phase materials, and are incorporated herein by reference thereto: Gleiter, H. (1989) "Nano-crystalline materials," Prog. Mater. Sci. 33:223-315 and Siegel, R. W. (1993) "Synthesis and properties of nano-phase materials," Mater. Sci. Eng. A168:189-197. In certain embodiments, the nanoparticles comprise oxides or nitrides of the following: silicon carbide, aluminum, diamond, cerium, carbon black, carbon nanotubes, zirconium, barium, cerium, cobalt, copper, europium, gadolinium, iron, nickel, samarium, silicon, silver, titanium, zinc, boron, and mixtures thereof. In certain embodiments, the nanoparticles of the present invention are selected from diamonds, zirconium oxide (amorphous, monoclinic, tetragonal and cubic forms), titanium oxide (amorphous, anatase, brookite and rutile forms), aluminum (amorphous, alpha, and gamma forms), and boronitride (cubic form). In particular embodiments, the nanoparticles of the present invention are selected from nano-diamonds, silicon carbide, titanium dioxide (anatase form), cubic-boronitride, and any combination thereof. Moreover, in particular embodiments, the nanoparticles can be crystalline or amorphous. In particular embodiments, the nanoparticles are less than or equal to 100 mm in diameter, e.g., less than or equal to 50 mm in diameter, e.g., less than or equal to 20 mm in diameter.

Moreover, it should be understood that the nanoparticles that are characterized as dispersed within the composites of the invention are intended to describe exogenously added nanoparticles. This is in contrast to nanoparticles, or formations containing significant similarity with putative nanoparticles, that are capable of formation in situ, wherein, for example, macromolecular structures, such as particles, can comprise an aggregation of these endogenously created.

The term "substantially disordered" refers to a lack of pore ordering based on x-ray powder diffraction analysis. Specifically, "substantially disordered" is defined by the lack of a peak at a diffraction angle that corresponds to a d value (or d-spacing) of at least 1 nm in an x-ray diffraction pattern.

"Surface modifiers" include (typically) organic functional groups which impart a certain chromatographic functionality to a chromatographic stationary phase. The porous inorganic/organic hybrid materials possess both organic groups and silanol groups which can additionally be substituted or derivatized with a surface modifier.

The language "surface modified" is used herein to describe the composite material of the present invention that possess both organic groups and silanol groups which can additionally be substituted or derivatized with a surface modifier. "Surface modifiers" include (typically) organic functional groups which impart a certain chromatographic functionality to a chromatographic stationary phase. Surface modifiers such as disclosed herein are attached to the base material, e.g., via derivatization or coating and later cross-linking, imparting the chemical character of the surface modifier to the base material. In one embodiment, the organic groups of a hybrid material react to form an organic covalent bond with a surface modifier. The modifiers can form an organic covalent bond to the material's organic group via a number of mechanisms well known in organic and polymer chemistry including but not limited to nucleophilic, electrophilic, cycloaddition, free-radical, carbene, nitrene, and carbocation reactions. Organic covalent bonds are defined to involve the formation of a covalent bond between the common elements of organic chemistry including but not limited to hydrogen, boron, carbon, nitrogen, oxygen, silicon, phosphorus, sulfur, and the halogens. In addition, carbon-silicon and carbon-oxygen-silicon bonds are defined as organic covalent bonds, whereas silicon-oxygen-silicon bonds that are not defined as organic covalent bonds. A variety of synthetic transformations are well known in the literature, see, e.g., March, J. *Advanced Organic Chemistry*, 3rd Edition, Wiley, New York, 1985.

Chromatographic Materials

Chromatographic materials of the present invention can include those comprising a silica core material, metal oxide core material, an inorganic-organic hybrid material or a group of block copolymers thereof core material. The core material can be a high purity chromatographic core composition as discussed herein. Similarly, the chromatographic core material can be a regular, e.g., not high purity, version/analog/homolog of the high purity materials discussed herein.

Examples of suitable core materials include, but are not limited to, conventional chromatographic silica materials, metal oxide materials, inorganic-organic hybrid materials or a group of block copolymers thereof, ceramic, silicon oxide, silicon imidonitride, silicon nitride, silicon aluminum nitride, silicon diimide, and silicon oxynitride. Additional examples of suitable core materials (for use with or without modification) are described in US Pub. Nos. 2009/0127177, 2007/0135304, 2009/0209722, 2007/0215547, 2007/0141325, 2011/0049056, 2012/0055860, and 2012/0273404 as well as International Pub. No. WO2008/103423, which are incorporated herein by reference in their entirety.

The chromatographic core material can be in the form of discreet particles or can be a monolith. The chromatographic core material can be any porous material and can be commercially available or can be produced by known methods, such as those methods described in, for example, in U.S. Pat. Nos. 4,017,528, 6,528,167, 6,686,035 and 7,175,913, which are incorporated herein by reference in their entirety. In some embodiments, the chromatographic core material can be a non-porous core.

The composition of the chromatographic surface material and the chromatographic core material can be varied by one of ordinary skill in the art to provide enhanced chromatographic selectivity, enhanced column chemical stability, enhanced column efficiency, and/or enhanced mechanical strength. Similarly, the composition of the surrounding material provides a change in hydrophilic/lipophilic balance (HLB), surface charge (e.g., isoelectric point or silanol $pK_a$), and/or surface functionality for enhanced chromatographic separation. Furthermore, in some embodiments, the composition of the chromatographic material can also provide a surface functionality for available for further surface modification.

The ionizable groups and the hydrophobic surface groups of the chromatographic materials of the invention can be prepared using known methods. Some of the ionizable modifier reagents are commercially available. For example silanes having amino alkyl trialkoxysilanes, methyl amino alkyl trialkoxysilanes, and pyridyl alkyl trialkoxysilanes are commercially available. Other silanes such as chloropropyl alkyl trichlorosilane and chloropropyl alkyl trialkoxysilane are also commercially available. These can be bonded and reacted with imidazole to create imidazolyl alkyl silyl surface species, or bonded and reacted with pyridine to create pyridyl alkyl silyl surface species. Other acidic modifiers are also commercially available, including, but not limited to, sulfopropyltrisilanol, carboxyethylsilanetriol, 2-(carbomethoxy)ethylmethyldichlorosilane, 2-(carbomethoxy)ethyltrichlorosilane, 2-(carbomethoxy)ethyltrimethoxysilane, n-(trimethoxysilylpropyl)ethylenediamine, triacetic acid, (2-diethylphosphatoethyl)triethoxysilane, 2-(chlorosulfonylphenyl)ethyltrichlorosilane, and 2-(chlorosulfonylphenyl)ethyltrimethoxysilane.

It is known to one skilled in the art to synthesize these types of silanes using common synthetic protocols, including Grinard reactions and hydrosilylations. Products can be purified by chromatography, recrystallization or distillation.

Other additives such as isocyanates are also commercially available or can be synthesized by one skilled in the art. A common isocyanate forming protocol is the reaction of a primary amine with phosgene or a reagent known as triphosgene.

In one aspect, the present invention provides a chromatographic stationary phase material for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography represented by Formula 1: [X](W)a(Q)b(T)c (Formula 1). X can be a high purity chromatographic core composition having a surface comprising a silica core material, metal oxide core material, an inorganic-organic hybrid material or a group of block copolymers thereof. W can be absent and/or can include hydrogen and/or can include a hydroxyl on the surface of X. Q can be a functional group that minimizes retention variation over time (drift) under chromatographic conditions utilizing low water concentrations. T can include one or more hydrophilic, polar, ionizable, and/or charged functional groups that chromatographically interact with the analyte. Additionally, b and c can be positive numbers, with the ratio $0.05 \leq (b/c) \leq 100$, and $a \geq 0$.

In another aspect, the present invention provides a chromatographic stationary phase material represented by Formula 1: [X](W)a(Q)b(T)c (Formula 1). X can be a chromatographic core material including a silica based, metal oxide based, or inorganic-organic hybrid based core surface. W can be absent and/or can include hydrogen and/or can include hydroxyl on the surface of X. Q can include one or more functional groups that essentially prevent chromatographic interaction between an analyte, and X and W, such that a first fraction of Q is bound to X and a section fraction of Q is polymerized. T can include one or more hydrophilic, polar, ionizable, and/or charged functional groups that chromatographically interact with the analyte, such that a third fraction of T is bound to Q, a fourth fraction of T is bound to X, and a fourth fraction of T is polymerized. Additionally, b and c can be positive numbers, with the ratio $0.05 \leq (b/c) \leq 100$, and $a \geq 0$.

In various embodiment, the selectivity of a chromatographic material can be controlled or influenced through the selection of Q and/or T, the density of Q and/or T on the surface, or a combination thereof.

In various embodiments, the invention provides a bonded chromatographic material to which ligands can be attached. The high density coverage attained by the bonding method of the invention can be 2X to 3X higher than silane bonding chemistries currently practiced in conventional SFC materials. A combination of high coverage and the other properties of Q and/or T can prevent the interaction of surface silanols with analytes.

In various embodiments, the invention provides high density of bonded phases increases retention and prevents retention drift or change caused by analyte interactions with surface silanols or other secondary retention mechanisms. Elimination of these secondary and minor selectivity components greatly improves peak shape and column peak capacity, especially for basic analytes.

In various embodiments, the invention provides for the use of a coupling chemistry based two component system produces an even coverage of mixed surface functionality. Unlike mixed particle beds where two separate particles with different surface chemistries are mixed this material has an even, and predictable, surface character throughout. A column packed with such material is not prone to chromatographic instability due to poor particle mixing or particle type segregation during column packing.

In various embodiments, the invention provides for column packing that is simplified due to the use of a single particle slurry.

In various embodiments, the invention provides for a chromatographic packing material with enhanced selectivity for acidic, neutral and basic analytes in a single column without the use of a mixed or multiple particle based bed.

In various embodiments, the invention provides for a ratio of the components on the particle surface that can be easily manipulated to alter the selectivity of the support providing a wide range of options for chromatographic separation.

In various embodiments, the invention provides for bonding chemistry whereby the formation of a crosslinked film of the silane surface modifying agent either through polymerization of the surface reactive groups or by the addition of a cross linking agent either before during or after the addition of the selectivity ligand.

In certain other embodiments, the chromatographic material of the invention is non-porous. In another embodiment, the chromatographic material of the invention is hydrolytically stable at a pH of about 1 to about 14; at a pH of about 10 to about 14; or at a pH of about 1 to about 5.

In another aspect, the invention provides materials as described herein wherein the chromatographic material further comprises a nanoparticle or a mixture of more than one nanoparticles dispersed within the chromatographic surface. In certain embodiments, the nanoparticle is present in <20% by weight of the nanocomposite, <10% by weight of the nanocomposite, or <5% by weight of the nanocomposite.

In other embodiments, the nanoparticle is crystalline or amorphous and can be silicon carbide, aluminum, diamond, cerium, carbon black, carbon nanotubes, zirconium, barium, cerium, cobalt, copper, europium, gadolinium, iron, nickel, samarium, silicon, silver, titanium, zinc, boron, oxides thereof, or a nitride thereof. In particular embodiments, the nanoparticle is a substance which comprises one or more moieties selected from the group consisting of nano-diamonds, silicon carbide, titanium dioxide, and cubic-boronitride. In other embodiments, the nanoparticles can be less than or equal to 200 nm in diameter, less than or equal to 100 nm in diameter, less than or equal to 50 nm in diameter, or less than or equal to 20 nm in diameter.

Preparation of Chromatographic Materials

The invention includes methods of producing the materials (e.g., the chromatographic materials) of the present invention. In various aspects and embodiments, the invention includes chemically modifying chromatographic core materials (e.g., as described above), to prepare chromatographic materials that mitigate or avoid retention drift or change. The concept of chemically modifying chromatographic core materials, as used herein, is understood to include functionalizing a chromatographic core, for example with a polar silane, or other functional group, thereby mitigating or avoiding retention drift or change. For example, functionalization can essentially prevent chromatographic interaction between an analyte and the chromatographic core (e.g., effectively eliminating a chromatographic effect of core surface silanols and/or alkoxylated silanols). In some cases, functionalization (e.g., using nonpolar groups) can reduce the retentivity of the column. Therefore, in various embodiments functionalization of chromatographic core materials can include the use of hydrophilic, polar, ionizable, and/or charged functional group that chromatographically interacts with the analyte, to preserve or achieve a chromatographically useful overall retention. Such endcapping groups can be introduced, for example, via standard bonding chemistry.

In some embodiments, functionalization provides a permanent attachment. Accordingly, it is important to select an appropriate functionalization for the chromatographic phase. In preferred embodiments, the chromatographic material will have chromatographically desirable properties (e.g., overall retention). Therefore in some embodiments it is important to select a functionalization that has properties that can mimic the desirable (e.g., overall retention) properties of a conventional chromatographic material.

In various embodiments, the chemical properties of a functional group can be selected to achieve a desired effect. For example, one or more hydrophilic, polar, ionizable, and/or charged functional group can be used to achieve desired interactions with an analyte (e.g., chromatographically acceptable retention) and/or the mobile phase (e.g., repelling alcohols that might alkoxylate a chromatographic core surface). Likewise, endcap size and/or sterics can be selected to mask a core surface and/or effect a chiral separation.

Similarly, the concentration of functionalization can be varied. In some embodiments, larger and/or more strongly interacting functional groups can mitigate or avoid retention drift or change at lower concentrations (e.g., as compared to smaller functional groups). In other embodiments, coverage can be tailored for a desired property. For example, nonpolar functional groups can be used at lower coverage than polar functional groups (e.g., to maintain a desired retention). In various embodiments, functionalization can use one or more polar or nonpolar endcaps, or a combination thereof. In some embodiments, surface area of the chromatographic media is increased or decreased to compensate for decreased or increased retention due to the altered polarity of the functional groups.

In one aspect, the present invention provides a chromatographic stationary phase material for normal phase chromatography, high-pressure liquid chromatography, solvated gas chromatography, supercritical fluid chromatography, subcritical fluid chromatography, carbon dioxide based chromatography, hydrophilic interaction liquid chromatography or hydrophobic interaction liquid chromatography represented by Formula 1: $[X](W)_a(Q)_b(T)_c$ (Formula 1). X can be a high purity chromatographic core composition having a surface including a silica core material, metal oxide core material, an inorganic-organic hybrid material or a group of block copolymers thereof. W can be absent and/or can include hydrogen and/or can include a hydroxyl on the surface of X. Q can be a functional group that minimizes retention variation over time (drift) under chromatographic conditions utilizing low water concentrations. T can include one or more hydrophilic, polar, ionizable, and/or charged functional groups that chromatographically interact with the analyte. Additionally, b and c can be positive numbers, with the ratio $0.05 \leq (b/c) \leq 100$, and $a \geq 0$.

In another aspect, the present invention provides a chromatographic stationary phase material represented by Formula 1: $[X](W)_a(Q)_b(T)_c$ (Formula 1). X can be a chromatographic core material including a silica based, metal oxide based, or inorganic-organic hybrid based core surface. W can be absent and/or can include hydrogen and/or can include hydroxyl on the surface of X. Q can include one or more functional groups that essentially prevent chromatographic interaction between an analyte, and X and W, such that a first fraction of Q is bound to X and a section fraction of Q is polymerized. T can include one or more hydrophilic, polar, ionizable, and/or charged functional groups that chromatographically interact with the analyte, such that a third fraction of T is bound to Q, a fourth fraction of T is bound to X, and a fourth fraction of T is polymerized. Additionally, b and c can be positive numbers, with the ratio $0.05 \leq (b/c) \leq 100$, and $a \geq 0$.

In one or more embodiments, Q is represented by:

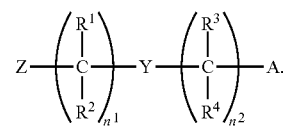

In one or more embodiments, $n^1$ is an integer from 0-30 and $n^2$ is an integer from 0-30. Each occurrence of $R^1$, $R^2$, $R^3$ and $R^4$ can independently represent hydrogen, fluoro, methyl, ethyl, n-butyl, t-butyl, i-propyl, lower alkyl, a protected or deprotected alcohol, a zwitterion, or a group Z. In some embodiments, group Z includes a surface attachment group having the formula $(B^1)_x(R^5)_y(R^6)_z Si—$, wherein x is an integer from 1-3, y is an integer from 0-2, z is an integer from 0-2, and $x+y+z=3$. Each occurrence of $R^5$ and $R^6$ can independently represent methyl, ethyl, n-butyl, iso-butyl, tert-butyl, iso-propyl, thexyl, substituted or unsubstituted aryl, cyclic alkyl, branched alkyl, lower alkyl, a protected or deprotected alcohol, or a zwitterion group and $B^1$ can represent a siloxane bond. In some embodiments, group Z includes an attachment to a surface organofunctional hybrid group through a direct carbon-carbon bond formation or through a heteroatom, ester, ether, thioether, amine, amide, imide, urea, carbonate, carbamate, heterocycle, triazole, or urethane linkage. In some embodiments, group Z includes an adsorbed, surface group that is not covalently attached to the surface of the material. Y can be an embedded polar functionality. In some embodiments, A represents a hydrophilic terminal group. In some embodiments, A represents hydrogen, fluoro, methyl, ethyl, n-butyl, t-butyl, i-propyl, lower alkyl, or group Z. In some embodiments, A represents a functionalizable group.

In one or more embodiments, T is represented by one of:

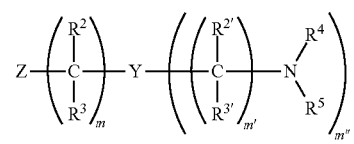

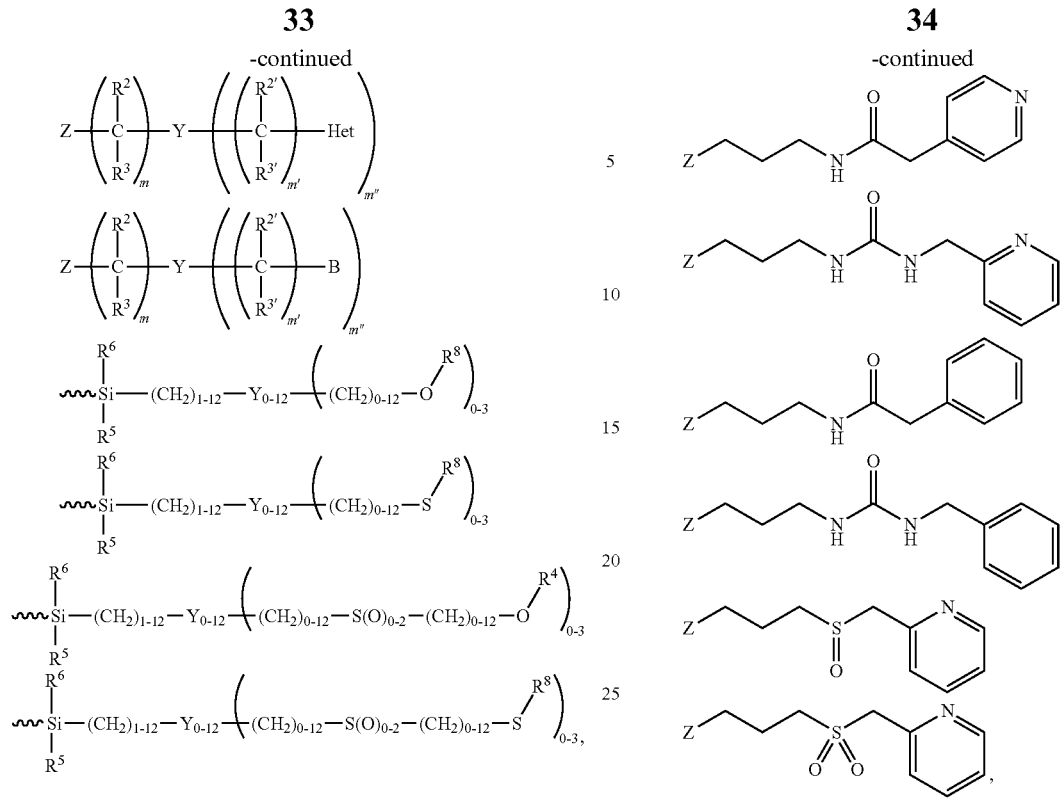

or a combination thereof. In some embodiments, m is an integer from 0-30; m' is an integer from 0-30; and m" is an integer from 0-3. In some embodiments, Z represents a surface attachment group having the formula $(B^1)_x(R^5)_y(R^6)_z$Si—, wherein x is an integer from 1-3, y is an integer from 0-2, z is an integer from 0-2, and x+y+z=3. Each occurrence of $R^5$ and $R^6$ can independently represent methyl, ethyl, n-butyl, iso-butyl, tert-butyl, iso-propyl, thexyl, substituted or unsubstituted aryl, cyclic alkyl, branched alkyl, lower alkyl, a protected or deprotected alcohol, or a zwitterion group. $B^1$ can represent a siloxane bond; where each of $R^{7'}$ $R^{7''}$ and $R^{7'''}$ represents hydrogen, methyl, ethyl, n-butyl, iso-butyl, tert-butyl, iso-propyl, thexyl, phenyl, branched alkyl or lower alkyl. In some embodiments, Z represents an attachment to a surface organofunctional hybrid group through a direct carbon-carbon bond formation or through a heteroatom, ester, ether, thioether, amine, amide, imide, urea, carbonate, carbamate, heterocycle, triazole, or urethane linkage. In some embodiments, Z represents an adsorbed, surface group that is not covalently attached to the surface of the material.

In some embodiments, b and c are positive numbers, with a ratio 0.05≤(b/c)≤100, and a≥0. In some embodiments, Q and T are different, whereas in other embodiments Q and T are the same. Q can include two or more different moieties, and T can include two or more different moieties. In some embodiments, the first, second, third, fourth, and fifth fraction are each independently about 0-100, 1-99, 5-95, 10-90, 20-80, 30-70, 40-60, 0, 5, 10, 15, 20, 25, 30, 35, 40, 45, 50, 55, 60, 65, 70, 75, 80, 85, 90, or 95%.

In one or more embodiments, Q is non-polar. In some embodiments, Q comprises a borate or nitro functional group. In some embodiments, Q is represented by one of:

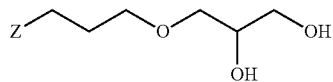

wherein Z can include a surface attachment group having the formula $(B^1)_x(R^5)_y(R^6)_z$Si—, wherein x is an integer from 1-3, y is an integer from 0-2, z is an integer from 0-2, and x+y+z=3. Each occurrence of $R^5$ and $R^6$ can independently represent methyl, ethyl, n-butyl, iso-butyl, tert-butyl, iso-propyl, thexyl, substituted or unsubstituted aryl, cyclic alkyl, branched alkyl, lower alkyl, a protected or deprotected alcohol, or a zwitterion group, and $B^1$ can represent a siloxane bond.

In another embodiment, Z is an attachment to a surface organofunctional hybrid group through a direct carbon-carbon bond formation or through a heteroatom, ester, ether, thioether, amine, amide, imide, urea, carbonate, carbamate, heterocycle, triazole, or urethane linkage. In yet another embodiment, Z is an adsorbed, surface group that is not covalently attached to the surface of the material.

In some embodiments, T is represented by one of:

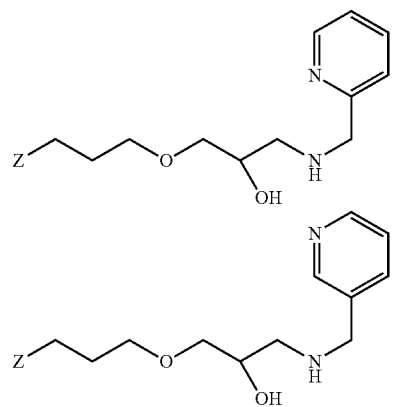

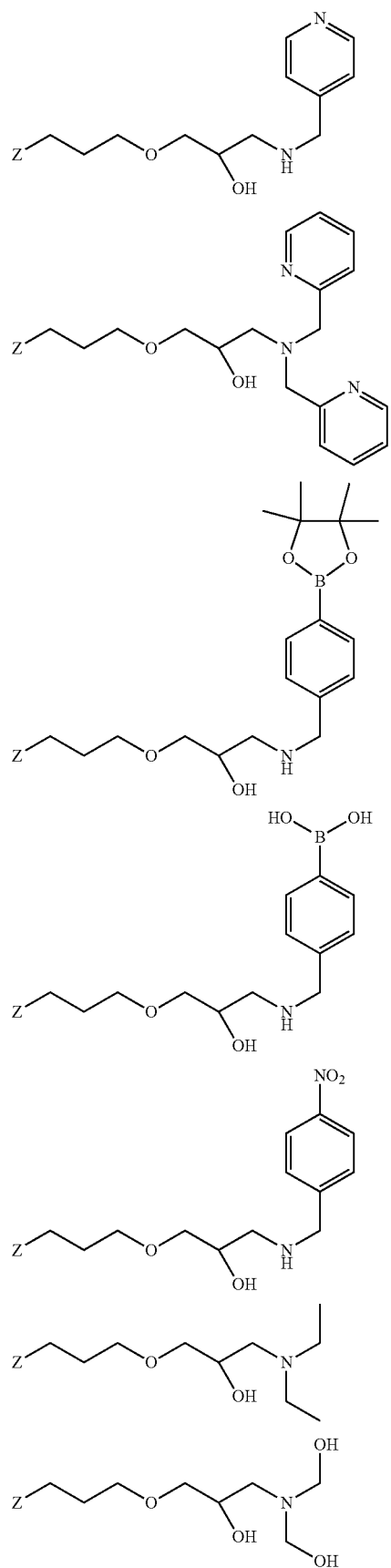
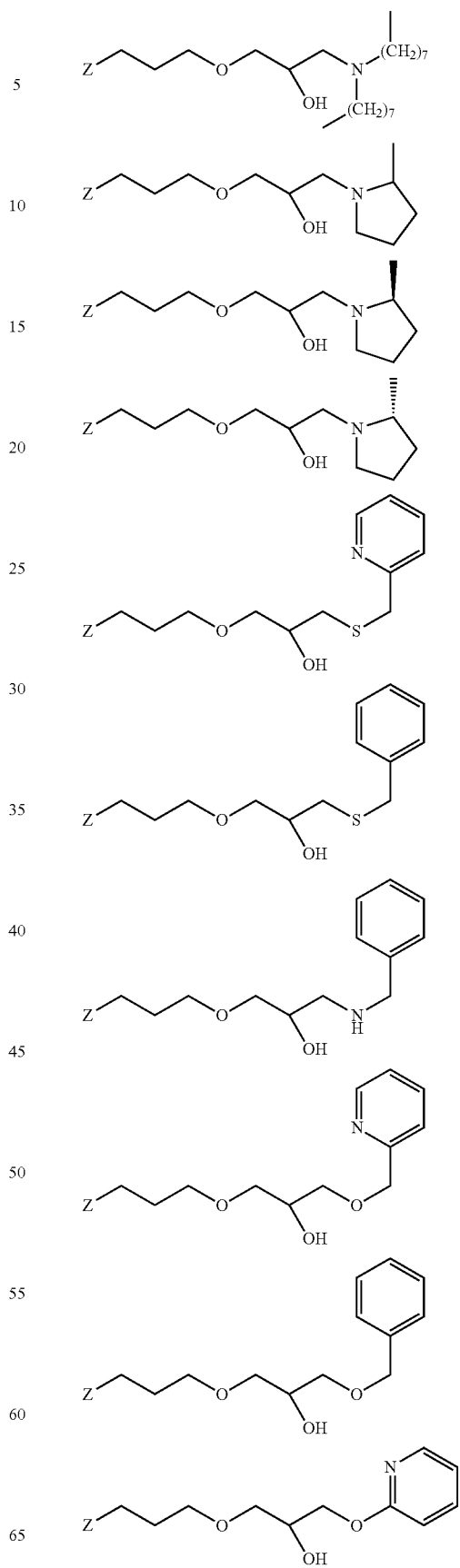

-continued

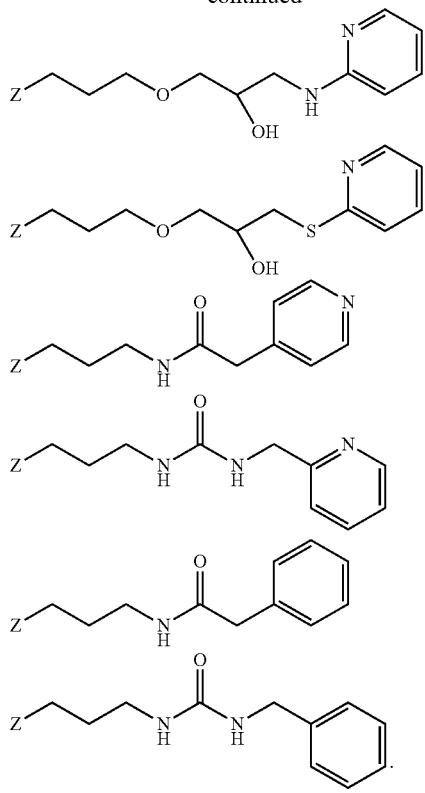

In some embodiments, Z includes a surface attachment group having the formula $(B^1)_x(R^5)_y(R^6)_z Si-$, wherein x is an integer from 1-3, y is an integer from 0-2, z is an integer from 0-2, and x+y+z=3. Each occurrence of $R^5$ and $R^6$ can independently represent methyl, ethyl, n-butyl, iso-butyl, tert-butyl, iso-propyl, thexyl, substituted or unsubstituted aryl, cyclic alkyl, branched alkyl, lower alkyl, a protected or deprotected alcohol, or a zwitterion group, and $B^1$ can represent a siloxane bond. In some embodiments, Z is an attachment to a surface organofunctional hybrid group through a direct carbon-carbon bond formation or through a heteroatom, ester, ether, thioether, amine, amide, imide, urea, carbonate, carbamate, heterocycle, triazole, or urethane linkage. In some embodiments, Z is an adsorbed, surface group that is not covalently attached to the surface of the material.

In one or more embodiments of any of the above aspects, X is a high purity chromatographic material having a core surface that is subject to alkoxylation by a chromatographic mobile phase under chromatographic conditions. X can be a chromatographic material having a core surface that is subject to alkoxylation by a chromatographic mobile phase under chromatographic conditions. In some embodiments, the functional group including Q is a diol. The functional group including T can be an amine, an ether, a thioether, or a combination thereof. T can include a chiral functional group adapted for a chiral separation, Q can include a chiral functional group adapted for a chiral separation, or T and Q can both include a chiral functional group adapted for a chiral separation.

In one or more embodiments of the above aspects, the ratio b/c is about 0.05-75, 0.05-50, 0.1, 0.2, 0.3, 0.4, 0.5, 0.6, 0.7, 0.8, 0.9, 1, 5, 10, 15, 20, 25, 30, 35, 40, 45, 50, 60, 70, 80, or 90. In some embodiments, the surface of X does not include silica, and b=0 or c=0. In some embodiments, the combined surface coverage is greater than about 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.4, 3.5, 3.6, 3.7, 3.8, 3.9, 4, 5, 6, 7, or 8 µmol/m².

In some embodiments of the above aspects, the chromatographic stationary phase exhibits a retention drift or change of ≤5% over 30 days, ≤4% over 30 days, ≤3% over 30 days, ≤2% over 30 days, ≤1% over 30 days, ≤5% over 10 days, ≤4% over 10 days, ≤3% over 10 days, ≤2% over 10 days, ≤1% over 10 days, ≤5% over 3 days, ≤4% over 3 days, ≤3% over 3 days, ≤2% over 3 days, ≤1% over 3 days, ≤5% over 30 runs, ≤4% over 30 runs, ≤3% over 30 runs, ≤2% over 30 runs, ≤1% over 30 runs, ≤5% over 10 runs, ≤4% over 10 runs, ≤3% over 10 runs, ≤2% over 10 runs, ≤1% over 10 runs, ≤5% over 3 runs, ≤4% over 3 runs, ≤3% over 3 runs, ≤2% over 3 runs, or ≤1% over 3 runs.

In some embodiments, the core material consists essentially of a silica material. Optionally, the core material consists essentially of an organic-inorganic hybrid material or a superficially porous material. In one or more embodiments, the core material consists essentially of an inorganic material with a hybrid surface layer, a hybrid material with an inorganic surface layer, a surrounded hybrid layer, or a hybrid material with a different hybrid surface layer. The stationary phase material can optionally be in the form of a plurality of particles, a monolith, or a superficially porous material. In some embodiments the stationary phase material does not have chromatographically enhancing pore geometry whereas in other embodiments the stationary phase material has chromatographically enhancing pore geometry. The stationary phase material can be in the form of a spherical material, non-spherical material (e.g., including toroids, polyhedrons). In certain embodiments, the stationary phase material has a highly spherical core morphology, a rod shaped core morphology, a bent-rod shaped core morphology, a toroid shaped core morphology; or a dumbbell shaped core morphology. In certain embodiments, the stationary phase material has a mixture of highly spherical, rod shaped, bent rod shaped, toroid shaped, or dumbbell shaped morphologies.

In some embodiments, the stationary phase material has a surface area of about 25 to 1100 m²/g, about 150 to 750 m²/g, or about 300 to 500 m²/g. In some embodiments, the stationary phase material has a pore volume of about 0.2 to 2.0 cm³/g, or about 0.7 to 1.5 cm³/g. In some embodiments, the stationary phase material has a micropore surface area of less than about 105 m²/g, less than about 80 m²/g, or less than about 50 m²/g. The stationary phase material can have an average pore diameter of about 20 to 1500 Å, about 50 to 1000 Å, about 60 to 750 Å, or about 65 to 200 Å. In some embodiments, the plurality of particles have sizes between about 0.2 and 100 microns, between about 0.5 and 10 microns, or between about 1.5 and 5 microns.

In one or more embodiments, X includes a silica core, c=0, and Q has a combined surface coverage of ≥2.5, 2.6, 2.7, 2.8, 2.9, 3.0, 3.5, 4.0, 4.5, or 5 µmol/m²; or X includes a non-silica core or a silica-organic hybrid core, c=0, and Q has a combined surface coverage of ≥0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5, or 5 µmol/m²; or b>0, c>0, and Q has a combined surface coverage of ≥0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, 4.0, 4.5, or 5 µmol/m².

The chromatographic stationary phase can be adapted for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography.

In yet another aspect, the present invention provides a chromatographic stationary phase material represented by Formula 1: $[X](W)_a(Q)_b(T)_c$ (Formula 1). X can be a chromatographic core material that is subject to retention drift or change under normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography conditions. W can be absent and/or can include hydrogen and/or can include hydroxyl on the surface of X. Q can include functional groups that essentially prevent chromatographic interaction between an analyte, and X and W. T can include functional groups that chromatographically interact with the analyte, and is bound to X through Q. "b" and "c: can be positive numbers, such that $0.05 \leq (b/c) \leq 100$, and $a \geq 0$.

In some embodiments, the chromatographic stationary phase material is adapted for normal phase chromatography, supercritical fluid chromatography, subcritical fluid chromatography, carbon dioxide based chromatography, hydrophobic interaction liquid chromatography, high pressure liquid chromatography, solvated gas chromatography, or a combination thereof.

In some embodiments, the chromatographic stationary phase includes radially adjusted pores, non-radially adjusted pores, ordered pores, non-ordered pores, monodispersed pores, non-monodispersed pores, smooth surfaces, rough surfaces or combinations thereof. In one or more embodiments, T has one ionizable group, T has more than one ionizable group, T has two or more ionizable groups of the same pKa, or T has two or more ionizable group of different pKa.

In yet another aspect, the present invention provides a column, capillary column, microfluidic device or apparatus for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography. The column, capillary column, microfluidic device or apparatus includes a housing having at least one wall defining a chamber having an entrance and an exit, and a stationary phase including any of the chromatographic materials of the present disclosure disposed therein. The housing and stationary phase can be adapted for normal phase chromatography, supercritical fluid chromatography, carbon dioxide based chromatography, or hydrophobic interaction liquid chromatography.

In yet another aspect, the present invention provides a kit for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography. The kit can include a housing having at least one wall defining a chamber having an entrance and an exit, and a stationary phase according to any of the materials of the present invention disposed therein. The housing and stationary phase can be adapted for normal phase chromatography, supercritical fluid chromatography, carbon dioxide based chromatography, or hydrophobic interaction liquid chromatography. The kit can further include instructions for performing normal phase chromatography, supercritical fluid chromatography, carbon dioxide based chromatography, or hydrophobic interaction liquid chromatography with the housing and stationary phase.

In yet another aspect, the present disclosure provides a method for preparing a stationary phase including any of the materials of the present disclosure. The method includes reacting a core surface with a silane coupling agent having a pendant reactive group. The method further includes reacting a second chemical agent including one or more hydrophilic, polar, ionizable, and/or charged functional groups with the pendant reactive group. The method further includes neutralizing any remaining unreacted pendant reactive groups, thereby producing a stationary phase according to the present disclosure.

In yet another aspect, the present disclosure provides a method for preparing a stationary phase according to any of the materials of the present disclosure. The method includes oligomerizing a silane coupling agent having a pendant reactive group. The method further includes reacting a core surface with the oligomerized silane coupling agent. The method further includes reacting a second chemical agent including one or more hydrophilic, polar, ionizable, and/or charged functional groups with the pendant reactive group. The method further includes neutralizing any remaining unreacted pendant reactive groups, thereby producing a stationary phase according to the present disclosure.

In one or more embodiments, Q is derived from a reagent having one or the following structures:

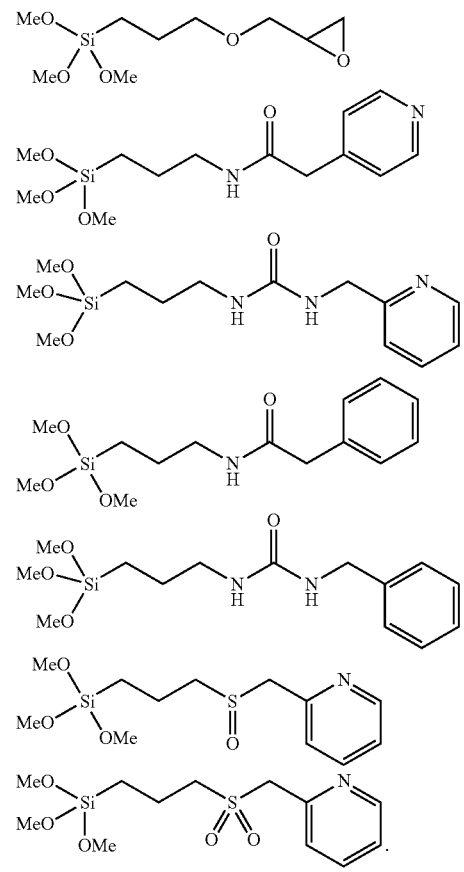

In some embodiments, T is derived from a reagent having one or the following structures:

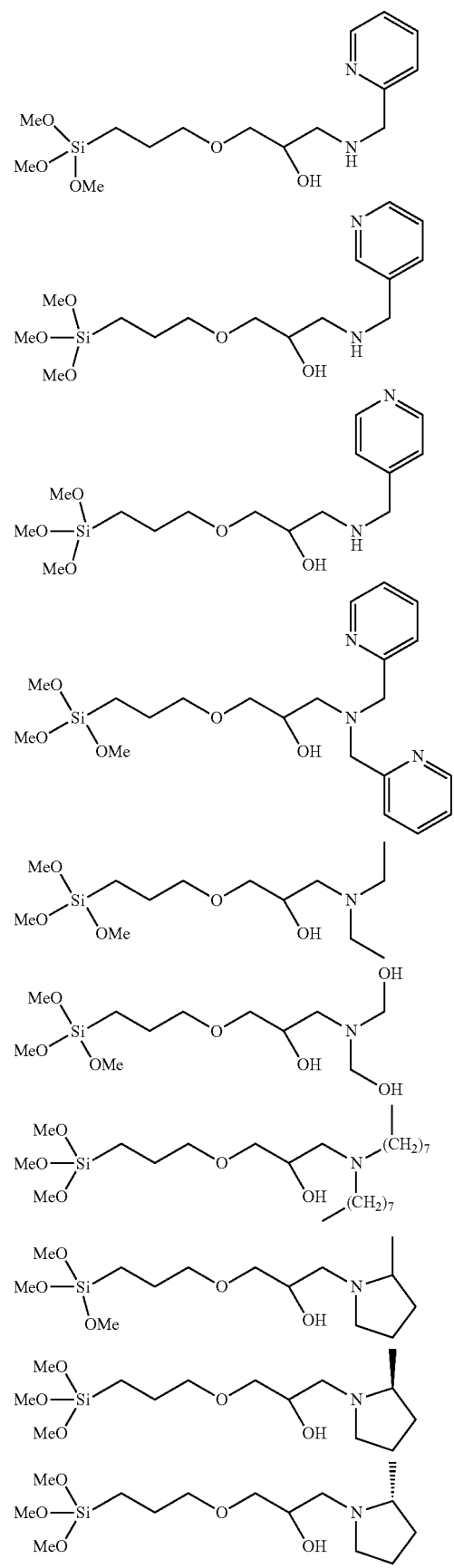
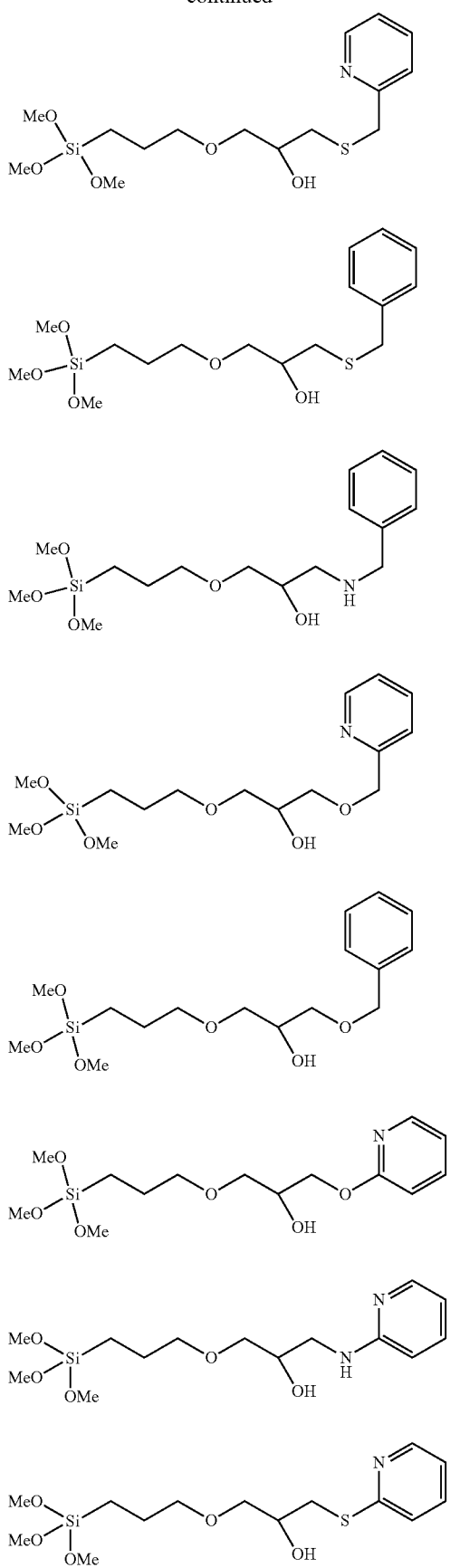

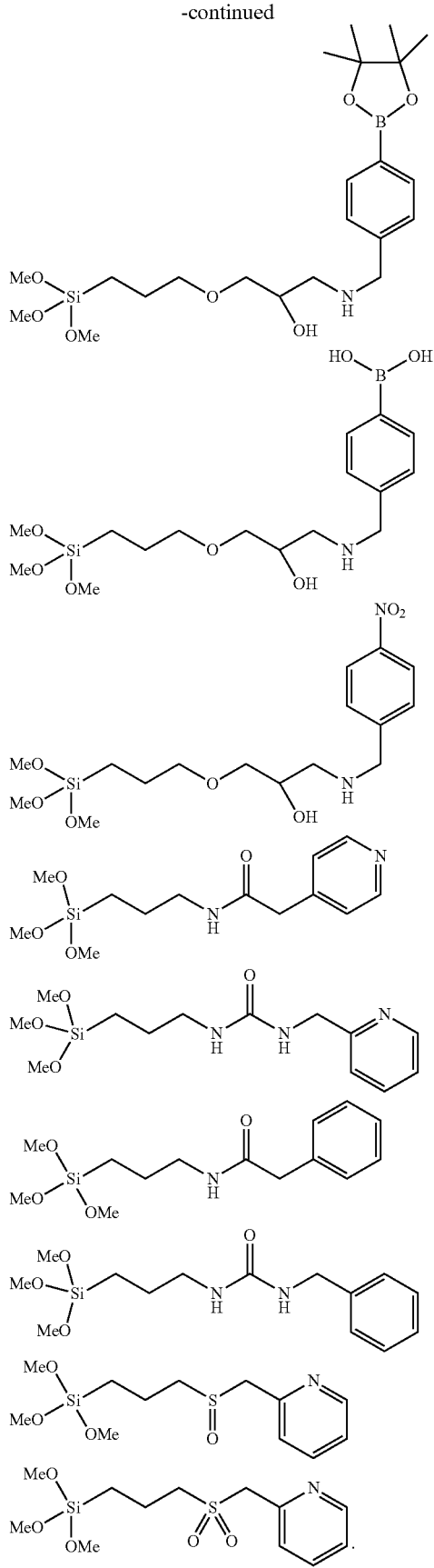

In yet another aspect, the invention provides a method for mitigating or preventing retention drift or change in normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography. The invention includes chromatographically separating a sample using a chromatographic device including a chromatographic stationary phase according to the present disclosure, thereby mitigating or preventing retention drift or change.

In one or more embodiments, mitigating or preventing retention drift or change includes a retention drift or change of ≤5% over 30 days, ≤4% over 30 days, ≤3% over 30 days, ≤2% over 30 days, ≤1% over 30 days, ≤5% over 10 days, ≤4% over 10 days, ≤3% over 10 days, ≤2% over 10 days, ≤1% over 10 days, ≤5% over 3 days, ≤4% over 3 days, ≤3% over 3 days, ≤2% over 3 days, ≤1% over 3 days, ≤5% over 30 runs, ≤4% over 30 runs, ≤3% over 30 runs, ≤2% over 30 runs, ≤1% over 30 runs, ≤5% over 10 runs, ≤4% over 10 runs, ≤3% over 10 runs, ≤2% over 10 runs, ≤1% over 10 runs, ≤5% over 3 runs, ≤4% over 3 runs, ≤3% over 3 runs, ≤2% over 3 runs, or ≤1% over 3 runs. In some embodiments, mitigating or preventing retention drift or change includes substantially eliminating the effect of alkoxylation and/or dealkoxylation of the chromatographic material on retention.

In some embodiments, T includes one of the following structures:

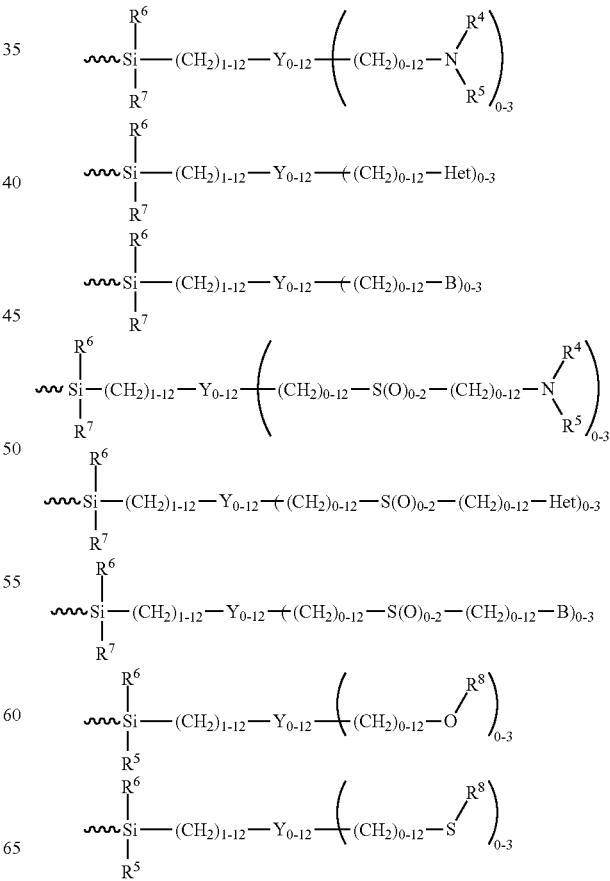

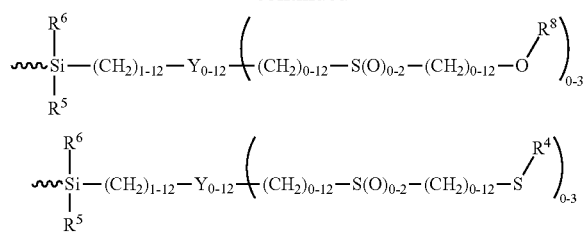
In some embodiments, Y includes one of the following structures:
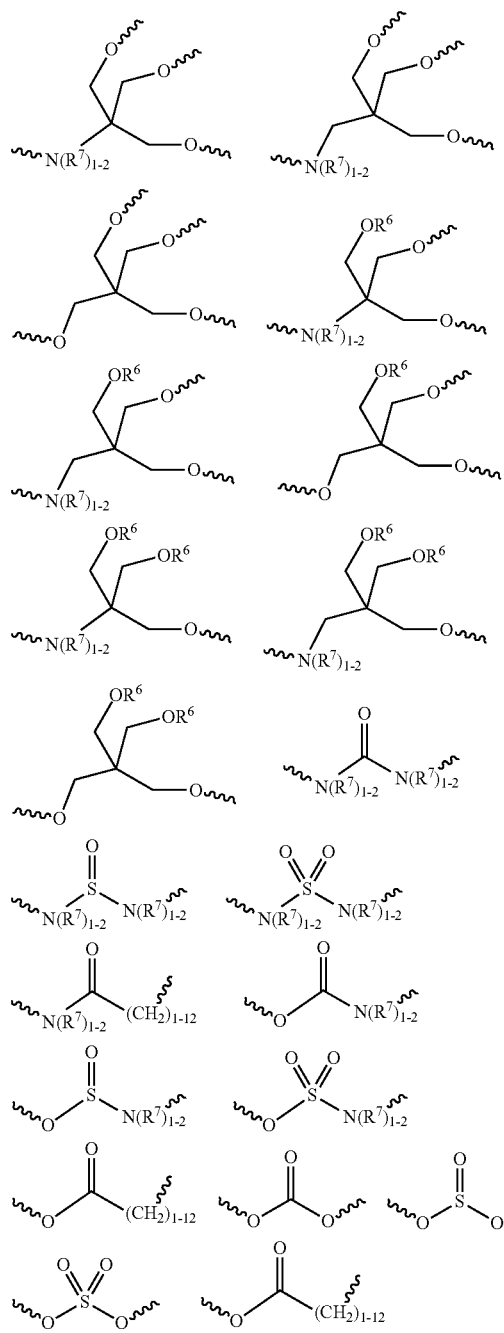
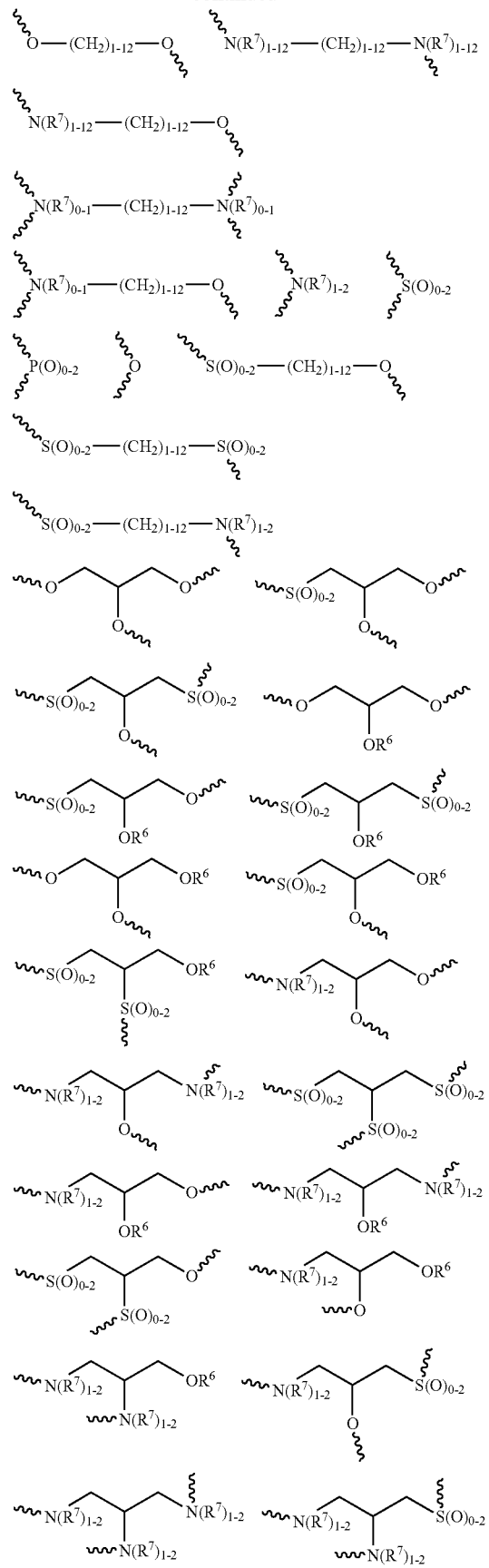

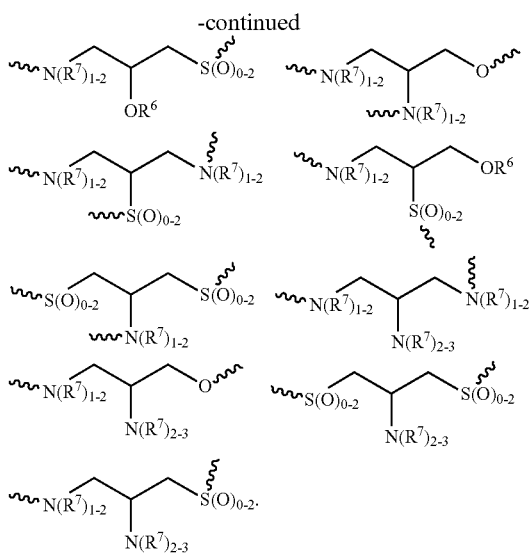

T can be derived from a reagent represented by:

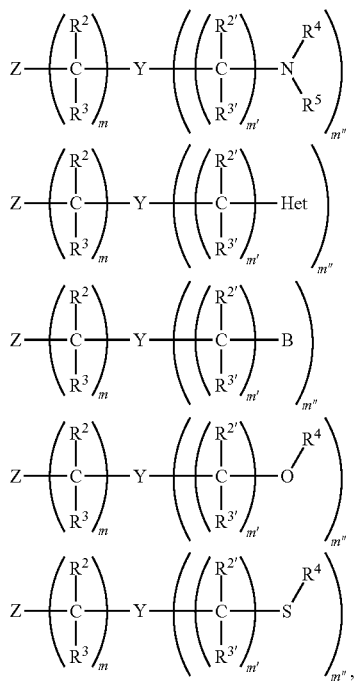

or a combination thereof, wherein m is an integer from 0-30; m' is an integer from 0-30; and m" is an integer from 0-3. Z can represent a chemically reactive group including:

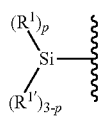

—$OR^6$, amine, alkylamine, dialkylamine, isocyanate, acyl chloride, triflate, isocyanate, thiocyanate, imidazole carbonate, NHS-ester, carboxylic acid, ester, epoxide, alkyne, alkene, azide, —Br, —Cl, or —I. Y can be an embedded polar functionality. Each occurrence of $R^1$ can independently represent a chemically reactive group on silicon, including (but not limited to) —H, —OH, —$OR^6$, dialkylamine, triflate, Br, Cl, I, vinyl, alkene, or —$(CH_2)_m Q$; Each occurrence of Q can be —OH, —$OR^6$, amine, alkylamine, dialkylamine, isocyanate, acyl chloride, triflate, isocyanate, thiocyanate, imidazole carbonate, NHS-ester, carboxylic acid, ester, epoxide, alkyne, alkene, azide, —Br, —Cl, or —I. p can be an integer from 1-3. Each occurrence of $R^{1'}$ can independently represent F, $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl, fluoroalkyl, or fluoroaryl. Each occurrence of $R^2$ and $R^3$ can independently represent hydrogen, $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl, —Z, or a group having the formula —$Si(R')_b R''_a$ or —$C(R')_b R''_a$. The variables a and b can each represent an integer from 0 to 3, provided that a+b=3. R' can represent a $C_1$-$C_6$ straight, cyclic or branched alkyl group. R" can be a functionalizing group selected from the group consisting of alkyl, alkenyl, alkynyl, aryl, cyano, amino, diol, nitro, ester, a cation or anion exchange group, an alkyl or aryl group containing an embedded polar functionality and a chiral moiety. $R^4$ can represent hydrogen, $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, substituted aryl, $C_5$-$C_{18}$ aryloxy, or $C_1$-$C_{18}$ heteroaryl. $R^5$ can represent hydrogen, $C_1$-$C_{15}$ alkyl, $C_2$-$C_{15}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, substituted aryl, $C_5$-$C_{18}$ aryloxy, or $C_1$-$C_{18}$ heteroaryl. Each occurrence of $R^6$ can independently represent $C_1$-$C_{18}$ alkyl, $C_2$-$C_{18}$ alkenyl, $C_2$-$C_{18}$ alkynyl, $C_3$-$C_{18}$ cycloalkyl, $C_1$-$C_{18}$ heterocycloalkyl, $C_5$-$C_{18}$ aryl, $C_5$-$C_{18}$ aryloxy, or $C_1$-$C_{18}$ heteroaryl. Het can represent a monocyclic or bicyclic heterocyclic or heteroaryl ring system including at least one nitrogen atom. B can represent an acidic ionizable modifier.

The above method can be used to make any of the materials (e.g., chromatography stationary phase materials) as described herein. For instance, the methods of the present invention can include methods of reacting a chromatographic stationary phase (e.g., silica particles) with a chemical reagent (e.g., any of the above reagents as described herein) to chemically modify the surface of the stationary phase to mitigate the effects of retention drift or change.

Apparatuses

The present invention include various apparatuses (e.g., chromatographic columns, capillary and microfluidic devices, and systems for use thereof) including the chromatographic materials described herein. While several illustrative examples are discussed below, a practitioner of ordinary skill will understand that the present invention can contemplate a number of different embodiments, including but not limited to chromatographic columns, apparatuses, methods of use, or kits.

In some embodiments, the invention provides a column or apparatus for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography, or a combination thereof. The column or apparatus includes a housing having at least one wall defining a chamber having an entrance and an exit, as well as a stationary phase according to any embodiments of the present invention disposed therein. The devices can have preformed frits, frits generated by interconnected materials, or devices without frits. The housing and stationary phase can be adapted for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography, or a combination thereof.

Accordingly, the apparatus of the present invention can contain (e.g., be packed with) materials of the present invention (e.g., a chromatographic stationary phase such as a chemically modified stationary phase adapted to reduce or mitigate retention drift or change). Moreover, the apparatus of the present invention can be used to carry out the methods of the present invention as described herein.

In one embodiment, the present invention is in the form a packed column. The column can be packed with a stationary phase (e.g., chromatographic material) described herein. Such a column can be used to perform different types of chromatography (e.g., normal phase chromatography, supercritical fluid chromatography, carbon dioxide based chromatography, hydrophobic interaction liquid chromatography, hydrophilic interaction liquid chromatography, sub-critical fluid chromatography, high pressure liquid chromatography, and solvated gas chromatography) while mitigating or avoiding retention drift or change.

The columns can be used in combination with existing chromatography platforms such as commercially available chromatography systems, including the Waters ALLIANCE® HPLC system, Waters ACQUITY® system, or Waters UPC²® system. A column of the present invention can be used for a number of different mass throughputs (e.g., analytical scale chromatography, preparative scale chromatography) while mitigating the effects of retention drift or change. Likewise, the present invention can be embodies in capillary and microfluidic devices, and systems (e.g., commercially available and know to persons of ordinary skill in the art) for use thereof. The selection of columns, capillary, and microfluidic devices, and related systems will be readily understandable to person of ordinary skill in the art.

Methods of Use

In one or more embodiments, the present invention offers methods of use. For instance, a skilled practitioner will understand that the present invention contemplates methods of use of the chromatographic stationary phases described in the present disclosure to mitigate the effects of retention drift or change when performing a chromatographic separation. The present invention can include methods of using the described stationary phase for different types of chromatographic separations, such as capillary scale separations, analytical separations, preparative scale separations, or industrial processing scale separations. The present invention can include methods of use of the present invention in various modes of chromatography, (e.g., HPLC, UHPLC, or SFC) to reduce retention drift or change.

In one or more embodiments, the present invention provides a method for mitigating or preventing retention drift or change in normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography, or a combination thereof. The method includes chromatographically separating a sample using a chromatographic device including a chromatographic stationary phase according to any embodiment of the present invention, thereby mitigating or preventing retention drift or change.

The methods can be performed using a kit of the present invention as described herein. Additionally, the method can be performed with an apparatus, column or materials (e.g., chromatographic stationary phase) of the present invention as describe herein. Moreover, the methods of the present invention can be used to analyze (e.g., detect the presence, quantity, concentration and the like) analytes of the present-ment invention.

The present invention can be used to separate and/or analyze a plurality of samples, including but not limited to small organic molecules, proteins, nucleic acids, lipids, fatty acids, carbohydrates, polymers, and the like. Similarly, the present invention can be used for the separation of small molecules, polar small molecules, analytes used in pharmaceuticals, biomolecules, antibodies, polymers and oligomers, sugars, glycan analysis, petrochemical analysis, lipid analysis, peptides, phosphopeptides, oligonucleotides, DNA, RNA, polar acids, polyaromatic hydrocarbons, food analysis, chemical analysis, bioanalysis, drugs of abuse, forensics, pesticides, agrochemicals, biosimilars, formulations.

In various embodiments, material in accordance with the present invention can have application in microbore columns for use on a SFC, HPLC, and/or UHPLC system.

In various embodiments, material in accordance with the present invention can have application fast equilibration columns, long lifetime columns, and SFC with water stable columns Kits The present invention provides a kit for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography, or a combination thereof. The kit can include a housing having at least one wall defining a chamber having an entrance and an exit, and a stationary phase according to any embodiments of the present invention disposed therein. The devices can have preformed frits, frits generated by interconnected materials, or devices without frits. The housing and stationary phase can be adapted for normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography, or a combination thereof. Additionally, instructions for performing normal phase chromatography, high-pressure liquid chromatography, solvated gas chromatography, supercritical fluid chromatography, sub-critical fluid chromatography, carbon dioxide based chromatography, hydrophilic interaction liquid chromatography or hydrophobic interaction liquid chromatography, or a combination thereof with the housing and stationary phase can be included.

Accordingly, the kit of the present invention can be used to implement the methods of the invention described herein. Additionally, the kits of the present invention can be used to analyze a variety of different samples and sample types, including those described herein below.

In one or more embodiments, the present invention can contemplate kits containing aspects of the present disclosure to reduce or mitigate the effects of retention drift or change. For instance, a kit can contain a chromatography column packed with a stationary phase media of the present disclosure. In some embodiments the packed column can be used directly in a standard chromatography system (e.g., a commercially available chromatography system such as a Waters ACQUITY® chromatography system). A kit can further contain instruction for use. Additionally, a kit can further contain stock samples of pure analyte for calibration of the instrument and/or confirmation of a substantial lack of retention drift or change. A kit can include any or all of the components described above (e.g., a stationary phase, a packed column, or a chromatography apparatus) to mitigate the effects of retention drift or change.

Analytes

Analytes amenable to chromatographic separation with the present invention can include essentially any molecule of interest, including, for example, small organic molecules, lipids, peptides, nucleic acids, synthetic polymers. The target analyte can be of interest, for example, in one or more of clinical chemistry, medicine, veterinary medicine, forensic chemistry, pharmacology, food industry, safety at work, and environmental pollution.

Clinical chemistry target analytes can include any molecule present in an organism (e.g., human body, animal body, fungi, bacterium, virus, and the like). For example, clinical chemistry target analytes include, but are not limited to, proteins, metabolites, biomarkers, and drugs.

Human medicine and veterinary medicine target analytes can include any molecule that can be used for the diagnosis, prophylaxis or treatment of a disease or condition in a subject. For example, human medicine and veterinary medicine target analytes include, but are not limited to, disease markers, prophylactic agents, or therapeutic agents.

Forensic chemistry target analytes can include any molecule present in a sample taken from the site of crime, such as a sample from a victim's body (e.g., tissue or fluid sample, hair, blood, semen, urine, and the like). For example, clinical chemistry target analytes include, but are not limited to, toxic agents, drugs and their metabolites, biomarkers, and identifying compounds.

Pharmacology target analytes can include any molecule that is a pharmaceutical or metabolite thereof or which can be used for the design, synthesis, and monitoring of drugs. For example, pharmacology target analytes include, but are not limited to, prophylactic and/or therapeutic agents, their prodrugs, intermediates and metabolites. Pharmacological analysis can include bioequivalence testing, for example, in connection with the approval, manufacturing, and monitoring of a generic drug.

Food industry and agricultural target analytes can include any molecule that is relevant for monitoring of the safety of foods, beverages, and/or other food industry/agricultural products. Examples of target analytes from the field of food industry include, but are not limited to, pathogen markers, allergens (e.g., gluten and nut proteins), and mycotoxins.

Target analytes can include polypeptides (e.g., polymers of naturally and/or non-naturally occurring amino acids such as Gly, Ala, Val, Leu, Ile, Pro, Phe, Trp, Cys, Met, Ser, Thr, Tyr, His, Lys, Arg, Asp, Glu, Asn, Gln, selenocysteine, ornithine, citrulline, hydroxyproline, methyllysine, carboxyglutamate), peptides, proteins, glycoproteins, lipoproteins; peptide-nucleic acids; hormones (such as peptide hormones (e.g., TRH and vasopressin), as well as synthetic and industrial polypeptides.

Samples

In general, a sample is a composition including at least one target analyte (e.g., an analyte of the class or kind disclosed above, together with a matrix). Samples can include a solid, liquid, gas, mixture, material (e.g., of intermediary consistency, such as an extract, cell, tissue, organisms) or a combination thereof. In various embodiments, the sample is a bodily sample, an environmental sample, a food sample, a synthetic sample, an extract (e.g., obtained by separation techniques), or a combination thereof.

Bodily samples can include any sample that is derived from the body of an individual. In this context, the individual can be an animal, for example a mammal, for example a human. Other example individuals include a mouse, rat, guinea-pig, rabbit, cat, dog, goat, sheep, pig, cow, or horse. The individual can be a patient, for example, an individual suffering from a disease or being suspected of suffering from a disease. A bodily sample can be a bodily fluid or tissue, for example taken for the purpose of a scientific or medical test, such as for studying or diagnosing a disease (e.g., by detecting and/or identifying a pathogen or the presence of a biomarker). Bodily samples can also include cells, for example, pathogens or cells of the individual bodily sample (e.g., tumour cells). Such bodily samples can be obtained by known methods including tissue biopsy (e.g., punch biopsy) and by taking blood, bronchial aspirate, sputum, urine, faeces, or other body fluids. Exemplary bodily samples include humour, whole blood, plasma, serum, umbilical cord blood (in particular, blood obtained by percutaneous umbilical cord blood sampling (PUBS), cerebrospinal fluid (CSF), saliva, amniotic fluid, breast milk, secretion, ichor, urine, faeces, meconium, skin, nail, hair, umbilicus, gastric contents, placenta, bone marrow, peripheral blood lymphocytes (PBL), and solid organ tissue extract.

Environmental samples can include any sample that is derived from the environment, such as the natural environment (e.g., seas, soils, air, and flora) or the manmade environment (e.g., canals, tunnels, buildings). Exemplary environmental samples include water (e.g., drinking water, river water, surface water, ground water, potable water, sewage, effluent, wastewater, or leachate), soil, air, sediment, biota (e.g., soil biota), flora, fauna (e.g., fish), and earth mass (e.g., excavated material).

Food samples can include any sample that is derived from food (including beverages). Such food samples can be used for various purposes including, for example, (1) to check whether a food is safe; (2) to check whether a food contained harmful contaminants at the time the food was eaten (retained samples) or whether a food does not contain harmful contaminants; (3) to check whether a food contains only permitted additives (e.g., regulatory compliance); (4) to check whether it contains the correct levels of mandatory ingredients (e.g., whether the declarations on the label of the food are correct); or (5) to analyze the amounts of nutrients contained in the food. Exemplary food samples include edible products of animal, vegetable or synthetic origin (e.g., milk, bread, eggs, or meat), meals, drinks, and parts thereof, such as retain samples. Food samples can also include fruits, vegetables, pulses, nuts, oil seeds, oil fruits, cereals, tea, coffee, herbal infusions, cocoa, hops, herbs, spices, sugar plants, meat, fat, kidney, liver, offal, milk, eggs, honey, fish, and beverages.

Synthetic samples can include any sample that is derived from an industrial process. The industrial process can be a biological industrial process (e.g., processes using biological material containing genetic information and capable of reproducing itself or being reproduced in a biological system, such as fermentation processes using transfected cells) or a non-biological industrial process (e.g., the chemical synthesis or degradation of a compound such as a pharmaceutical). Synthetic samples can be used to check and monitor the progress of the industrial process, to determine the yield of the desired product, and/or measure the amount of side products and/or starting materials.

EXAMPLES

Materials

All reagents were used as received unless otherwise noted. Those skilled in the art will recognize that equivalents of the following supplies and suppliers exist and, as such, the suppliers listed below are not to be construed as limiting.

Characterization

Those skilled in the art will recognize that equivalents of the following instruments and suppliers exist and, as such, the instruments listed below are not to be construed as limiting.

The % C values were measured by combustion analysis (CE-440 Elemental Analyzer; Exeter Analytical Inc., North Chelmsford, Mass.) or by Coulometric Carbon Analyzer (modules CM5300, CM5014, UIC Inc., Joliet, Ill.). Bromine and Chlorine content were determined by flask combustion followed by ion chromatography (Atlantic Microlab, Norcross, Ga.). The specific surface areas (SSA), specific pore volumes (SPV) and the average pore diameters (APD) of these materials were measured using the multi-point $N_2$ sorption method (Micromeritics ASAP 2400; Micromeritics Instruments Inc., Norcross, Ga.). The SSA was calculated using the BET method, the SPV was the single point value determined for $P/P_0 > 0.98$ and the APD was calculated from the desorption leg of the isotherm using the BJH method. The micropore surface area (MSA) was determined as the cumulative adsorption pore diameter data for pores <34 Å subtracted from the specific surface area (SSA). The median mesopore diameter (MMPD) and mesopore pore volume (MPV) were measured by Mercury Porosimetry (Micromeritics AutoPore II 9220 or AutoPore IV, Micromeritics, Norcross, Ga.). Skeletal densities were measured using a Micromeritics AccuPyc 1330 Helium Pycnometer (V2.04N, Norcross, Ga.). Particle sizes were measured using a Beckman Coulter Multisizer 3 analyzer (30 μm aperture, 70,000 counts; Miami, Fla.). The particle diameter ($dp_{50}$) was measured as the 50% cumulative diameter of the volume based particle size distribution. The width of the distribution was measured as the 90% cumulative volume diameter divided by the 10% cumulative volume diameter (denoted 90/10 ratio). Viscosity was determined for these materials using a Brookfield digital viscometer Model DV-II (Middleboro, Mass.). Measurements of pH were made with an Oakton pH100 Series meter (Cole-Palmer, Vernon Hills, Ill.) and were calibrated using Orion (Thermo Electron, Beverly, Mass.) pH buffered standards at ambient temperature immediately before use. Titrations were performed using a Metrohm 716 DMS Titrino autotitrator (Metrohm, Hersau, Switzerland), and are reported as milliequivalents per gram (mequiv/g). Coverage levels for the epoxide were determined by titrating the OH⁻ liberated upon addition of sodium thiosulfate. Multinuclear ($^{13}$C, $^{29}$Si) CP-MAS NMR spectra were obtained using a Bruker Instruments Avance-300 spectrometer (7 mm double broadband probe). The spinning speed was typically 5.0-6.5 kHz, recycle delay was 5 sec. and the cross-polarization contact time was 6 msec. Reported $^{13}$C and $^{29}$Si CP-MAS NMR spectral shifts were recorded relative to tetramethylsilane using the external standards adamantane ($^{13}$C CP-MAS NMR, δ 38.55) and hexamethylcyclotrisiloxane ($^{29}$Si CP-MAS NMR, δ −9.62). Populations of different silicon environments were evaluated by spectral deconvolution using DMFit software. [Massiot, D.; Fayon, F.; Capron, M.; King, I.; Le Calvé, S.; Alonso, B.; Durand, J.-O.; Bujoli, B.; Gan, Z.; Hoatson, G. *Magn. Reson. Chem.* 2002, 40, 70-76]

TABLE 1

Specific Base Particles Utilized

| Entry | Material |
|---|---|
| B1 | Hybrid Organic Silica (3.8 μm, 90 Å APD, 1.3 cm³/g TPV)[1] |
| B2 | Hybrid Organic Silica (3.8 μm, 115 Å APD, 1.3 cm³/g TPV)[1] |
| B3 | Hybrid Organic Silica (2.3 μm, 115 Å APD, 1.3 cm³/g TPV)[1] |

[1] As described in U.S Pat. No. 7,919,177, U.S. Pat. No. 7,223,473, U.S. Pat. No. 6,686,035 and WO2011084506

TABLE 2

List of Specific Nucleophiles Utilized

| Entry | Nucleophile |
|---|---|
| N1 | 2-picolylamine |
| N2 | 3-picolylamine |
| N3 | 4-picolylamine |
| N4 | Di-2-picolylamine |
| N5 | diethylamine |
| N6 | epinephrine |
| N7 | 3-(diethylamino)propylamine |
| N8 | 2-aminopyridine |
| N9 | 2-mercaptopyridine |
| N10 | benzylamine |
| N11 | 4-nitrobenzylamine |
| N12 | dioctylamine |
| N13 | 4-(aminomethyl)phenylboronic acid pinacol ester |
| N14 | (R)-2-methylpyrrolidine |

Embodiments of Specific Silanes Used

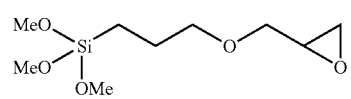

Glycidoxypropyltrimethoxysilane (GPTMS)

S1

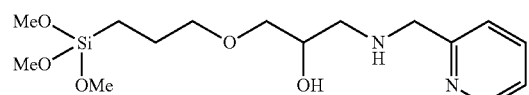

S2

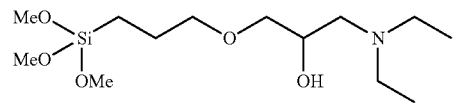

S3

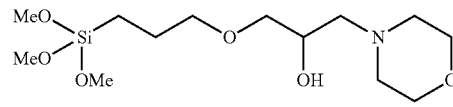

S4

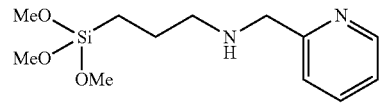

S5

-continued

S6

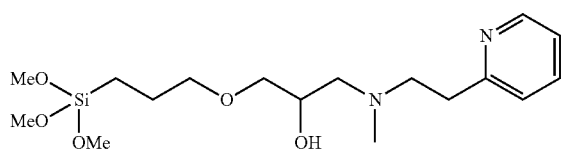

Example 1

In a typical reaction, hybrid porous particles were dispersed in a solution of glycidoxypropyltrimethoxysilane/methanol (0.25 mL/g) (GLYMO, Aldrich, Milwaukee, Wis.,) in a 20 mM acetate buffer (pH 5.5, prepared using acetic acid and sodium acetate, J. T. Baker. 5 mL/g dilution) that had be premixed at 70° C. for 60 minutes. The mixture was held at 70° C. for 20 hours. The reaction was then cooled and the product was filtered and washed successively with water and methanol (J. T. Baker). The product was then dried at 80° C. under reduced pressure for 16 hours. Reaction data is listed in Table 3. Specific changes to this general procedure include: 1) Material 1E was prepared utilizing a 6 hour reaction time, 2) Material 1F was prepared utilizing 100 mM acetate buffer, 3) Material 1G was prepared utilizing a 50° C. hold for 20 hours, 4) Material 1H was prepared utilizing a 50° C. premix and 50° C. hold.

Total surface coverages of 3.90-5.10 µmol/m² were determined by the difference in particle % C before and after the surface modification as measured by elemental analysis. Analysis of these materials by $^{13}$C CP-MAS NMR spectroscopy indicates a mixture of epoxy and diol groups are present for these materials.

TABLE 3

| | Base Material | | | Total | Coverage of |
|---|---|---|---|---|---|
| Example | Particle | Amount (g) | GPTMS Amount (g) | Coverage[1] (µmol/m²) | epoxide[2] (µmol/m²) |
| 1A | B1 | 70 | 90.7 | 3.90 | 1.52 |
| 1B | B2 | 40 | 39.0 | 4.80 | 1.86 |
| 1C | B3 | 25 | 23.4 | 4.76 | 1.76 |
| 1D | B2 | 20 | 17.3 | 4.71 | 1.67 |
| 1E | B2 | 60 | 52.1 | 4.73 | 3.11 |
| 1F | B2 | 20 | 19.3 | 4.87 | 1.51 |
| 1G | B2 | 20 | 19.3 | 5.10 | 2.38 |
| 1H | B2 | 20 | 19.3 | 4.22 | 3.23 |

[1]This refers to the combined coverage from the bonded GPTMS silane - coverage from unhydrolyzed epoxides + coverage from hydrolyzed epoxides (as the diol).
[2]As determined by titration.

Example 2

In a typical reaction, hybrid porous particles were dispersed in a solution of glycidoxypropyltrimethoxysilane/methanol (0.25 mL/g) (GLYMO, Aldrich, Milwaukee, Wis.) in a 20 mM acetate buffer (pH 5.5, prepared using acetic acid and sodium acetate, J. T. Baker. 5 mL/g dilution) w that had be premixed at 70° C. for 60 minutes. The mixture was held at 70° C. for 20 hours. The reaction was then cooled and the product was filtered and washed successively with water and methanol (J. T. Baker). The material was then refluxed in a 0.1 M acetic acid solution (5 mL/g dilution, J. T. Baker) at 70° C. for 20 hours. The reaction was then cooled and the product was filtered and washed successively with water and methanol (J. T. Baker). The product was then dried at 80° C. under reduced pressure for 16 hours. Reaction data is listed in Table 4. Surface coverages of 0.93-3.37 µmol/m² were determined by the difference in particle % C before and after the surface modification as measured by elemental analysis. Analysis of these materials by $^{13}$C CP-MAS NMR spectroscopy indicates no measurable amount of epoxide groups remain, having only diol groups present for these materials.

TABLE 4

| | Base Material | | | Total | Coverage of |
|---|---|---|---|---|---|
| Example | Particle | Amount (g) | GPTMS Amount (g) | Coverage[1] (µmol/m²) | epoxide[2] (µmol/m²) |
| 2A | B3 | 20 | 4.9 | 2.71 | N/A |
| 2B | B3 | 20 | 7.0 | 3.37 | N/A |
| 2C | B1 | 70 | 90.3 | 3.16 | N/A |
| 2D | B1 | 20 | 7.3 | 1.76 | N/A |
| 2E | B1 | 20 | 4.4 | 0.93 | N/A |

Example 3

In a standard experiment, 10 g of a material prepared as in Example 1 were dispersed in a solvent such as, but not limited to water, iso-propanol, or dioxane. An amount of nucleophile in excess of the epoxide coverage determined for the material from Example 1 was added and the mixture heated to 70° C. for 16 hours. Sulphur nucleophiles were coupled using 1 molar equivalent of an appropriate base. After reaction, the particles were washed successively with water and 0.5M acetic acid, and the material was then refluxed in a 0.1 M acetic acid solution (5 mL/g dilution, J. T. Baker) at 70° C. for 20 hours. The reaction was then cooled and the product was filtered and washed successively with water and methanol (J. T. Baker). The product was then dried at 80° C. under reduced pressure for 16 hours. Reaction data is listed in Table 5. Examples 3H, 3I and 3J utilized nucleophile charges lower than the determined expoxide coverages to achieve the reduced nucleophile surface concentrations. Nucleophile surface concentrations of 0.2-2.1 µmol/m² were determined by the difference in particle % C, % N or % S before and after the surface modification as measured by elemental analysis. Analysis of these materials by $^{13}$C CP-MAS NMR spectroscopy indicates no measurable amount of epoxide groups remain.

TABLE 5

| | Base Material | | |
|---|---|---|---|
| Example | Representative Preparation from Example 1 | Total Coverage from Initial Bonding (µmol/m²) | Nucleophile Used | Nucleophile Surface Concentration (µmol/m²) |
| 3A | 1B | 4.63 | N1 | 1.4 |
| 3B | 1B | 4.62 | N5 | 1.6 |
| 3C | 1B | 4.40 | N7 | 1.1 |
| 3D | 1B | 4.77 | N10 | 1.4 |
| 3E | 1C | 4.71 | N14 | 1.2 |
| 3F | 1C | 4.73 | N9 | 2.1 |
| 3G | 1C | 4.35 | N1 | 1.2 |
| 3H | 1C | 4.35 | N1 | 1.0 |
| 3I | 1C | 4.35 | N1 | 0.7 |
| 3J | 1C | 4.35 | N1 | 0.4 |
| 3K | 1C | 4.35 | N1 | 0.2 |
| 3L | 1A | 3.61 | N2 | 1.2 |
| 3M | 1A | 3.61 | N3 | 1.0 |
| 3N | 1A | 3.61 | N4 | 1.1 |

TABLE 5-continued

| | Base Material | | | |
|---|---|---|---|---|
| Example | Representative Preparation from Example 1 | Total Coverage from Initial Bonding (µmol/m$^2$) | Nucleophile Used | Nucleophile Surface Concentration (µmol/m$^2$) |
| 3O | 1B | 4.71 | N6 | 0.4 |
| 3P | 1C | 4.73 | N8 | 1.1 |
| 3Q | 1C | 4.73 | N12 | 1.2 |
| 3R | 1C | 4.95 | N13 | 1.8 |
| 3S | 1C | 4.95 | N11 | 1.4 |

Example 4

In a typical reaction, hybrid material (10 g) was refluxed in toluene (190 mL) using a Dean-Stark trap for 1 hour. Upon cooling, the desired silane and toluene (90 mL) were added to the flask. The mixture was stirred at room temperature for 1 hour, and then heated to reflux for 16 hours. The reaction was then cooled and the product was filtered and washed successively with toluene, acetone, 1:1 v/v acetone/water, and acetone (all solvents from Fisher Scientific). The particles were then slurried in a solution of acetone/0.1 M NH$_4$HCO$_3$ (60/40, v/v, 200 mL) and stirred for 20 hrs at 50° C. After cooling to room temperature, the particles were collected by filtration, and washed successively with 1:1 v/v acetone/water and acetone. The particles were dried overnight under vacuum at 80° C. Specific examples are presented in Table 6. Total surface coverages of 1.62-2.60 µmol/m$^2$ were determined by the difference in particle % C and/or % N before and after the surface modification as measured by elemental analysis.

TABLE 6

| | Base Material | | Silane | | |
|---|---|---|---|---|---|
| Example | Type | Amount (g) | Silane Used | Amount (g) | Coverage (µmol/m$^2$) |
| 4A | B1 | 15 | S2 | 12.6 | 2.08 |
| 4B | B1 | 10 | S3 | 7.5 | 1.97 |
| 4C | B1 | 20 | S4 | 15.7 | 1.62 |
| 4D | B1 | 20 | S5 | 13.2 | 2.60 |
| 4E | B1 | 10 | S6 | 9.1 | 1.89 |

Example 5

The general procedure for bondings/functionalization of particles that is detailed in Examples 1, 2 and 3 is applied to modify the surface silanol groups of different porous materials. Included in this are monolithic, spherical, granular, superficially porous and irregular materials that are silica, hybrid inorganic/organic materials, hybrid inorganic/organic surface layers on hybrid inorganic/organic, silica, titania, alumina, zirconia, polymeric or carbon materials, and silica surface layers on hybrid inorganic/organic, silica, titania, alumina, zirconia or polymeric or carbon materials. Also includes are stationary phase materials in the form of a spherical material, non-spherical material (e.g., including toroids, polyhedron); stationary phase materials having a highly spherical core morphology, a rod shaped core morphology, a bent-rod shaped core morphology, a toroid shaped core morphology; or a dumbbell shaped core morphology; and stationary phase materials having a mixture of highly spherical, rod shaped, bent rod shaped, toroid shaped, or dumbbell shaped morphologies. Example hybrid materials are shown in U.S. Pat. Nos. 4,017,528, 6,528,167, 6,686,035, and 7,175,913 as well as International Publication No. WO2008/103423, the contents of which are hereby incorporated by reference in their entireties. Superficially porous particle include those describe in U.S. Pub. Nos. 2013/0112605, 2007/0189944, and 2010/061367, the contents of which are hereby incorporated by reference in their entireties. The particles size for spherical, granular or irregular materials can vary from 5-500 µm; more preferably 15-100 µm; more preferably 20-80 µm; more preferably 40-60 µm. The APD for these materials can vary from 30 to 2,000 Å; more preferably 40 to 200 Å; more preferably 50 to 150 Å. The SSA for these materials can vary from 20 to 1000 m$^2$/g; more preferably 90 to 800 m$^2$/g; more preferably 150 to 600 m$^2$/g; more preferably 300 to 550 m$^2$/g. The TPV for these materials can vary from 0.3 to 1.5 cm$^3$/g; more preferably 0.5 to 1.4 cm$^3$/g; more preferably 0.7 to 1.3 cm$^3$/g. The macropore diameter for monolithic materials can vary from 0.1 to 30 µm, more preferably 0.5 to 25 µm, more preferably 1 to 20 µm.

Example 6

The general procedure for bondings/functionalization of particles that is detailed in Example 4 is applied utilizing mixtures of silanes in varying ratios. In particular, this procedure is applied to mixtures of silanes where one of the components is S1 and the other component(s) consist of silanes as defined by T and Q in the specification.

Example 7

The general procedure for bondings/functionalization of particles that is detailed in Example 2 is applied utilizing mixtures of different silanes in varying ratios. In particular, this procedure is applied to mixtures of silanes where one of the components is S1 and the other component(s) consist of silanes as defined by T and Q in the specification.

Example 8

Retention Change in Materials from Examples 2, 3 and 4

The average % retention change was calculated by taking the percent difference of the average absolute peak retentions measured from the day 3, 10 or 30 chromatographic tests from the average absolute peak retentions measured on the day one chromatographic test. For each day tested, the columns were equilibrated under Mix1 test conditions for 20 minutes followed by three injections of Mix1 and then equilibrated under Mix2 Test conditions for 10 minutes, followed by three injections of Mix2. Conditions are shown in Table 7. Results are shown in Tables 8, 9 and 10.

The % Less Retention was calculated by taking the percent difference of the day one average absolute peak retentions measured for Mix 1 and Mix 2 from the day one average absolute peak retentions measured for Mix 1 and Mix 2 on example 1A.

TABLE 7

Chromatographic Test Conditions for Retention Change Measurements

| | |
|---|---|
| Co-Solvent Mix 1 | 5% methanol |
| Sample Mix 1 | 3-benzoylpyridine (0.1 mg/mL) |
| Co-Solvent Mix 2 | 10% methanol |
| Sample Mix 2 | caffeine, thymine, papaverine, prednisolone, sulfanilamide |
| Column Dimension | 2.1 × 150 mm |
| Flow Rate | 1.0 mL/min |
| Column Temperature | 50° C. |
| Back Pressure | 1800 psi |
| Detector | ACQUITY ® PDA with SFC Flow Cell |
| Detector Setting | 254 nm 40 spec/sec |
| Weak Needle Wash | iso-propanol |
| Injection | 1.0 µL (2.0 µL loop with PLUNO injection mode) |

TABLE 8

Retention Change from Example 2 Materials Over Time

| | Average % Retention Change | | |
|---|---|---|---|
| Example | 3 Day Test | 10 Day Test | 30 Day Test |
| 2A | 0.0 | / | / |
| 2B | 0.2 | / | / |
| 2C | 0.2 | / | 1.8 |
| 2D | 3.1 | / | 1.2 |
| 2E | 0.4 | / | 0.2 |

/ indicates that this test was not performed for this material.

TABLE 9

Retention Change From Example 3 Materials Over Time

| | Average % Retention Change | | |
|---|---|---|---|
| Example | 3 Day Test | 10 Day Test | 30 Day Test |
| 2B | 0.8 | / | / |
| 2C | 0.0 | 0.6 | 0.7 |
| 2G | 0.2 | 1.6 | / |
| 2H | 0.7 | 2.0 | / |
| 2I | 0.2 | 0.6 | / |
| 2J | 0.4 | 2.0 | / |
| 2K | 1.3 | 2.2 | / |
| 2L | 1.0 | 1.6 | 0.4 |
| 2M | 0.5 | 0.0 | 1.1 |
| 2N | 2.4 | 1.1 | 1.0 |
| 2O | 0.2 | 2.3 | 2.9 |

/ indicates that this test was not performed for this material.

TABLE 10

Retention Change From Example 4 Materials Over Time

| | Average % Retention Change | | |
|---|---|---|---|
| Example | 3 Day Test | 10 Day Test | 30 Day Test |
| 4A | 0.1 | 0.9 | 4 |
| 4B | 0.8 | 2.1 | 5.4 |
| 4C | 5.3 | 7.1 | 11.2 |
| 4D | 4.3 | 6.5 | 10.2 |
| 4E | 5.0 | 6.2 | 10.0 |

Example 9

Surface Functionalization of Organic-Inorganic Hybrid Particles with Glycidoxypropyltrimethoxysilane (GPTMS) and 2-Picolylamine The structures of GPTMS and and 2-picolylamine are shown in FIG. 1. FIG. 1A shows the structure of GPTMS, a silane surface modifier. Part 105 shows the surface reactive group of GPTMS (trialkoxysilane), while part 110 shows the reactive group (epoxide). FIG. 1b shows the selectivity ligand (2-picolylamine).

The GPTMS is first allowed to pre form oligomers by pre incubation at 70° C. in 20 mM sodium Acetate buffer pH 5.0. During incubation small oligomers of the hydrolyzed silanes are formed. After a suitable pre incubation period the particles to be modified are added as a dry powder. The oligomers and any remaining monomer react with the material surface to produce a high surface coverage of silane modifier covalently attached to the material surface as shown in FIG. 2.

FIG. 2 shows a reaction of the silane coupling agent with the organic-inorganic hybrid material surface. The silane (205) is depicted as a monomer for simplicity. Pre formed oligomeric silanes can couple in the same manner as the surface reactive group (210). Under reaction conditions, methanol is lost (215) to give surface modified particles (220).

After the silane has reacted with the chromatographic material, excess reagents and buffer salts are removed by washing with MILLI-Q® water and the materials are transferred into an organic solvent (e.g., 1,4-dioxane) and the 2-picolylamine added. The amino group of the 2-picolylamine couples to the surface through the pendant epoxide groups of the GPTMS. The proportion of epoxy groups converted to 2-picolyl groups can be controlled by limiting the quantity of 2-picolylamine added. The coupled materials are then washed into 0.5M acetic acid and the unreacted epoxide groups hydrolyzed to the corresponding diol as shown in FIG. 3.

The resulting pyridyl/diol surface contains uniformly distributed pyridyl groups and provides excellent selectivity while the diol shields the surface silanols from interaction with analyte. The multicomponent surface is superior to the singular diol surface or the singular pyridyl surface.

Figure 3:
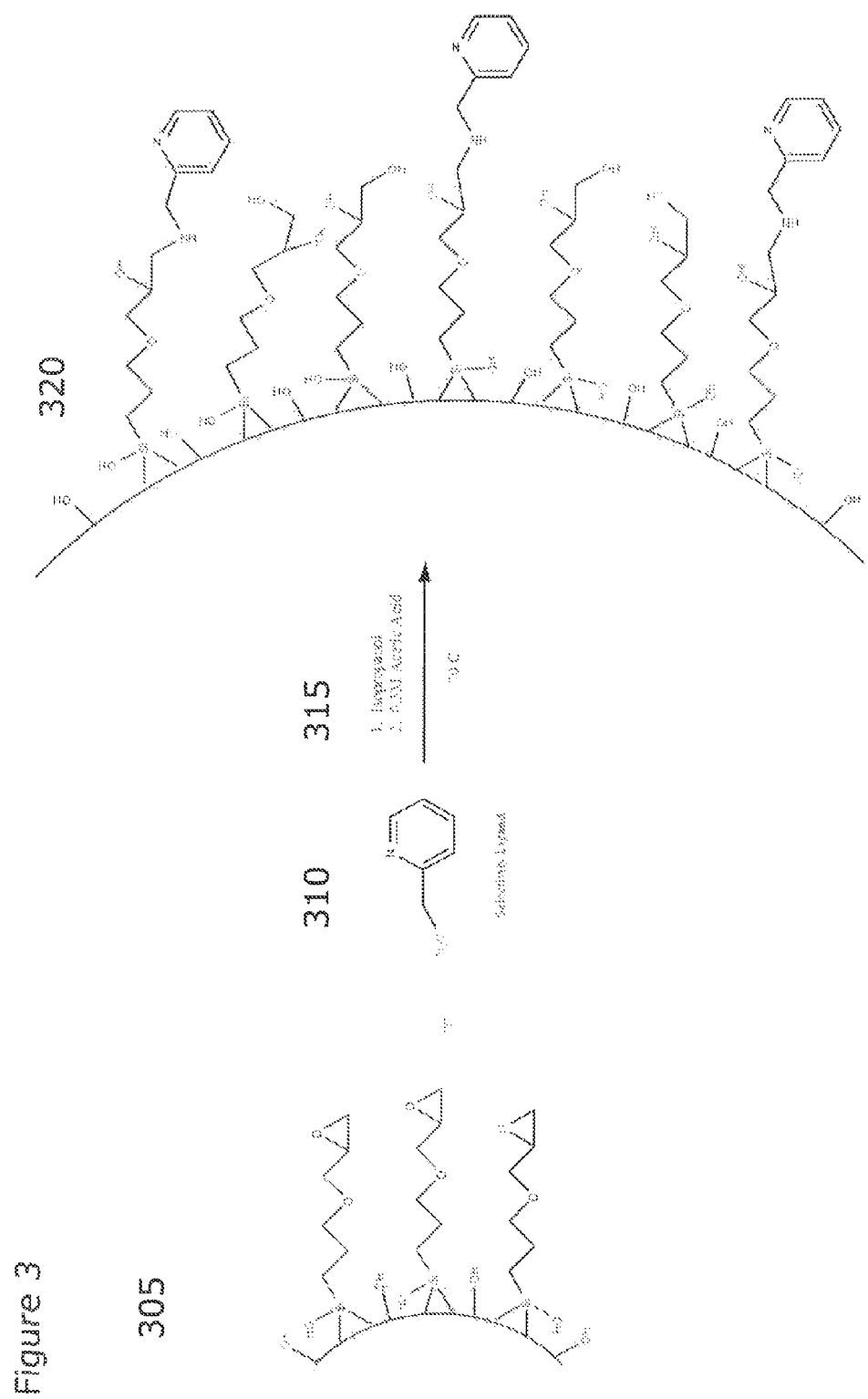
FIG. 3 shows a schematic of a reaction between a modified chromatographic surface and 2-picolylamine.

FIG. 3 shows reaction of the surface modified particle 305 with a selectivity ligand 310. The reaction conditions 315 are given and include treatment with isopropanol and 0.5M acetic acid at 70° C. The result is a stationary phase particle with a multicomponent surface for chromatographic separation (320).

Alternatively, the multicomponent surface can be produced under conditions which create a polymerized surface by using a silane coupling agent with a pendant reactive group as the bonded phase under reaction conditions that simultaneously bond to the base material surface, partially react the pendant reactive group to form inert pendant groups and also produce limited polymerization between pendant reactive groups on adjacent silane coupling agent molecules.

Figure 4:
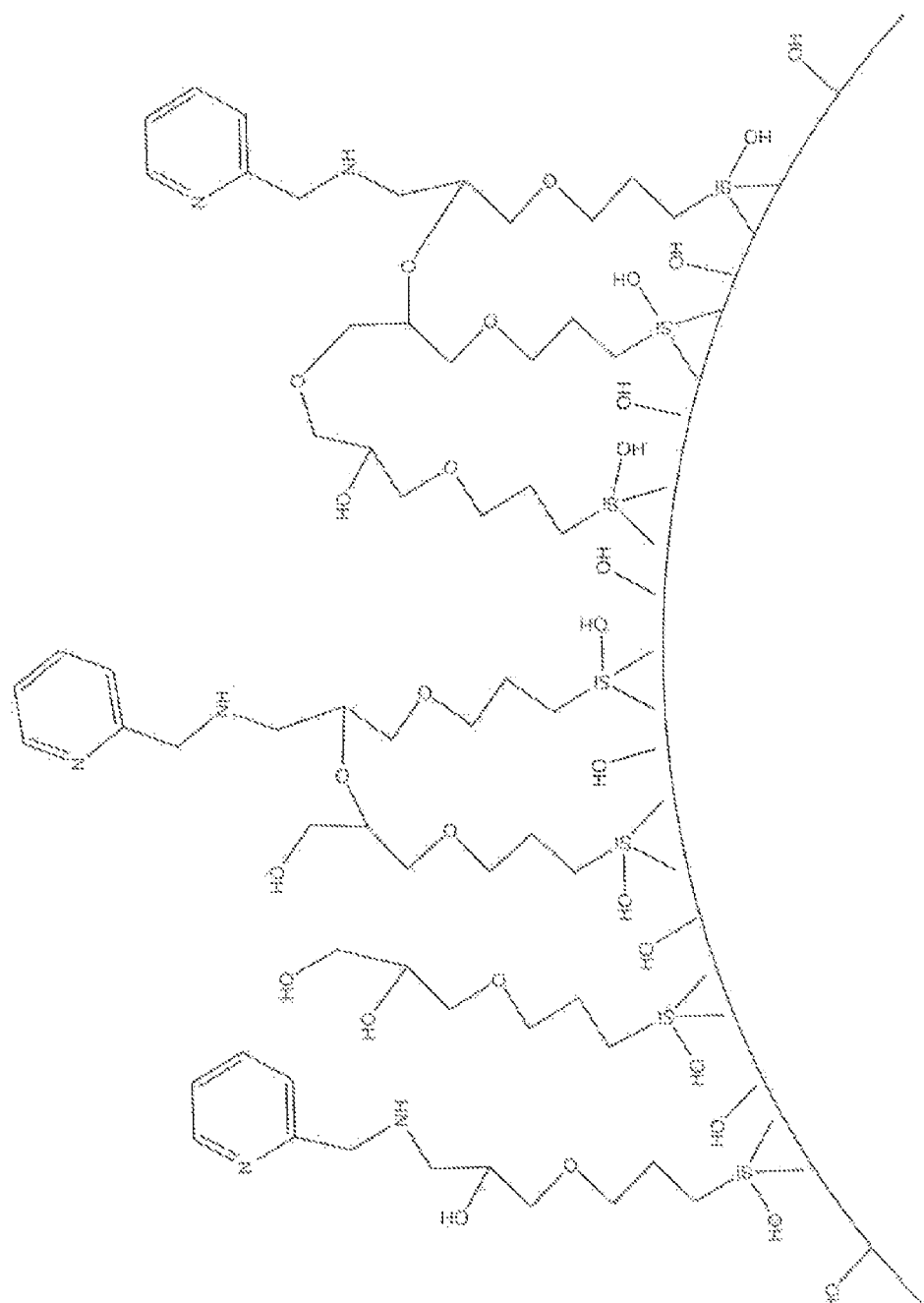
FIG. 4 shows a schematic of a chromatographic surface crosslinked with the modifying agents GPTMS and 2-picolylamine.

Similarly, the multicomponent surface can be produced under conditions which create a polymerized surface by covalently bonding a second chemical agent capable of interacting with an analyte to affect retention through introduction of charged, uncharged, polar, nonpolar, lipophilic or hydrophilic character to the chromatographic phase. Alternatively, under certain conditions the epoxy groups of GPTMS can react with the hydroxyl groups of adjacent silanes to form ether bridges which crosslink the GPTMS on the surface. Such cross linking can provide stability to the bonded phase and can also enhance silanol shielding. However, while the existence of such cross links is consistent with NMR analysis of these materials, it has not been conclusively proven as yet. An embodiment of the types of crosslinked surface is shown in FIG. 4. Such a structure would demonstrate the formation of ether bridges through polymerization of the surface epoxides.

Example 10

Figure 5:
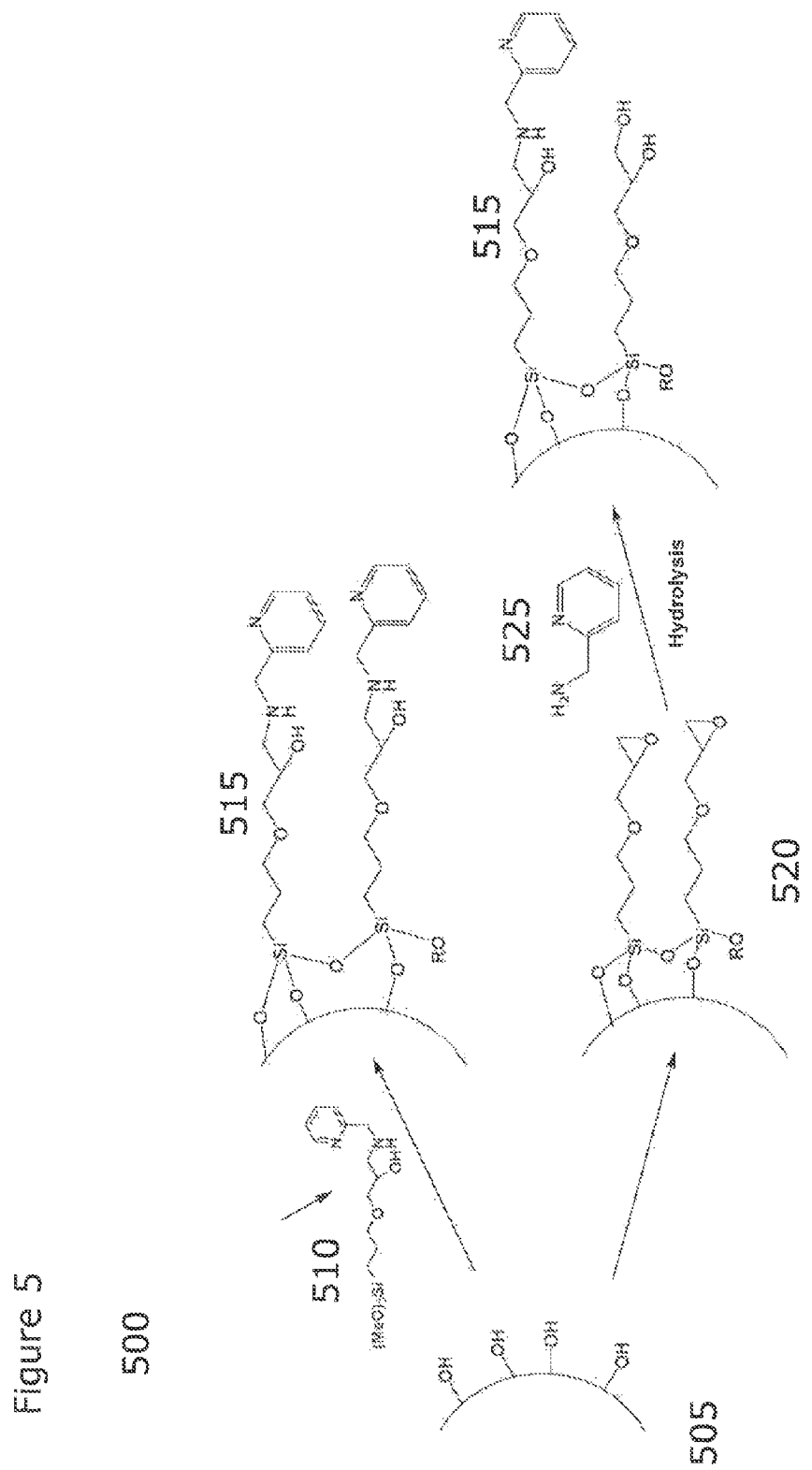
FIG. 5 shows a schematic of two potential synthetic routes to preparing a chromatographic stationary phase of the present disclosure.

FIG. 5 shows two potential synthetic routes to preparing a chromatographic stationary phase of the present disclosure. As shown in the scheme (500), an unmodified BEH particle (505) can be chemically modified in at least two different ways. Accordingly, one option, a chemical modifying agent (510) is first prepared by reacting GPTMS with 2-picolylamine. Reagent 510 is then reacted with the BEH particle (505) to give a functionalized chromatographic surface (515).

Alternatively, FIG. 5 shows a different synthetic route. In this embodiment, particle 505 is reacted directly with GPTMS to give a GPTMS-modified surface (520). Surface 520 can then be reacted with 2-picolylamine (525) to give a functionalized chromatographic surface (515). The overall yield is about 70%.

In a preferred embodiment, the second reaction pathway comprising first reacting particle 505 with GPTMS followed by functionalization with 2-picolylamine (525) is performed over the first reaction pathway comprising reacting particle 505 with a pre-formed chemical modifier 510.

Example 11

GPTMS Bonding on Organic-Inorganic Hybrid Mitigates Retention Drift or Change

Figure 6:
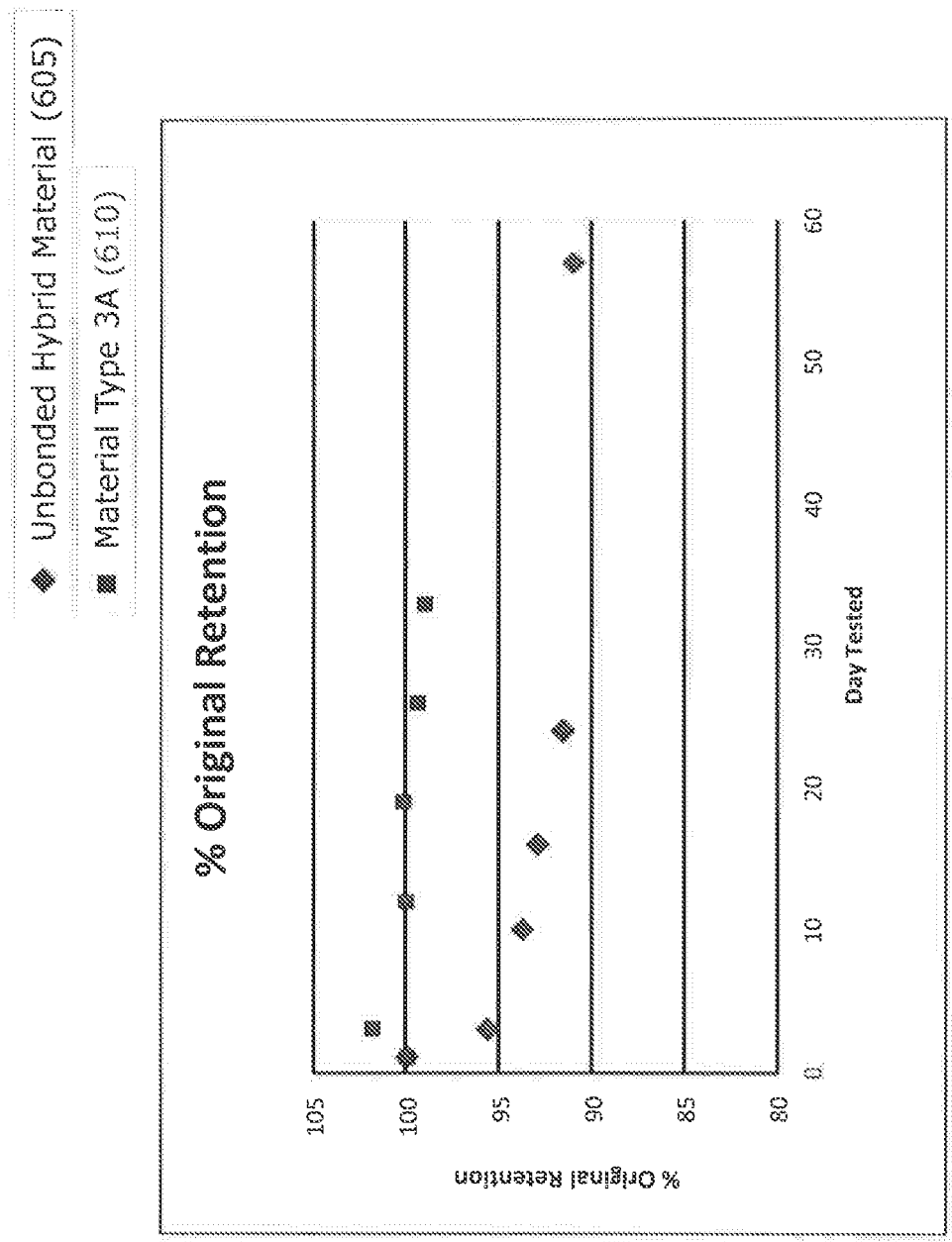
FIG. 6 shows a graph of the percent retention of an analyte eluted using unmodified BEH particles as a stationary phase, and BEH particles modified in accordance with the present specification as a stationary phase.

As shown in FIG. 6, treatment of a bridged ethylene hybrid (BEH) stationary phase with glycidoxypropyltrimethoxysilane (GPTMS) followed by a subsequent epoxide opening reaction to give a diol can significantly mitigate the effects of retention drift. Graph 600 shows a plot of the % Original Retention of unfunctionalized 3 μm BEH particles (605) compared with diol-functionalized 3 μm BEH particles (610). The % original retention is given as a function of time, with days on the x axis. The results indicate that, in at least some preferred embodiments, functionalizaiton of a chromatographic surface with GPTMS and subsequent epoxide opening to give a diol can mitigate retention drift. The results also show that the GPTMS coating alone addresses the issue of retention drift and also provides significant retention.

Unless indicated otherwise, all techniques, including the use of kits and reagents, can be carried out according to the manufacturers' information, methods known in the art.

Recitation of ranges of values herein is merely intended to serve as a shorthand method of referring individually to each separate value falling within the range. Unless otherwise indicated, each individual value is incorporated into the specification as if it were individually recited. Each of the documents cited herein (including all patents, patent applications, scientific publications, manufacturer's specifications, and instructions), are hereby incorporated by reference in their entirety.

The specification should be understood as disclosing and encompassing all possible permutations and combinations of the described aspects, embodiments, and examples unless the context indicates otherwise. One of ordinary skill in the art will appreciate that the invention can be practiced by other than the summarized and described aspect, embodiments, and examples, which are presented for purposes of illustration and not limitation.

The invention claimed is:
1. A method for mitigating or preventing retention drift in supercritical fluid chromatography, sub-critical fluid chromatography, or carbon dioxide based chromatography comprising:
chromatographically separating a sample using a chromatographic device comprising a chromatographic stationary phase represented by Formula 1:

$[X](W)_a(Q)_b(T)_c$           Formula 1 wherein:
X is a chromatographic core composition having a surface comprising a silica core material, metal oxide core material, an inorganic-organic hybrid material, or a group of block copolymers thereof;
W is an hydroxyl group on the surface of X;
Q is represented by:

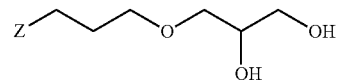

T is represented by one of:

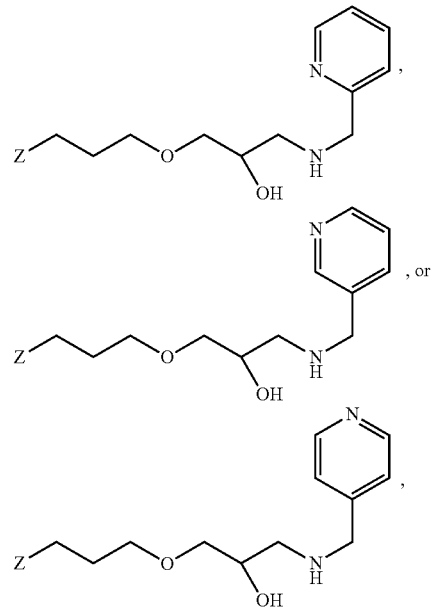

wherein each Z group independently comprises:
a) a surface attachment group having the formula $(B^1)_x(R^5)_y(R^6)_zSi-$
wherein x is an integer from 1-3,
y is an integer from 0-2,
z is an integer from 0-2,
and x+y+z=3 each occurrence of $R^5$ and $R^6$ independently represents methyl, ethyl, n-butyl, iso-butyl, tert-butyl, iso-propyl, substituted or unsubstituted aryl, cyclic alkyl, branched alkyl, lower alkyl, a protected or deprotected alcohol, or a zwitterion group; and $B^1$ represents a siloxane bond;

b) an attachment to a surface organofunctional hybrid group selected from the group consisting of a direct carbon-carbon bond, a heteroatom linkage, ester linkage, ether linkage, thioether linkage, amine linkage, amide linkage, imide linkage, urea linkage, carbonate linkage, carbamate linkage, heterocycle linkage, triazole linkage and urethane linkage; or c) an adsorbed, surface group that is not covalently attached to the surface of X; and b and c are positive numbers, $0.05 \leq (b/c) \leq 100$, and $a \geq 0$, thereby mitigating or preventing retention drift.

2. The method of claim 1, wherein T is represented by:

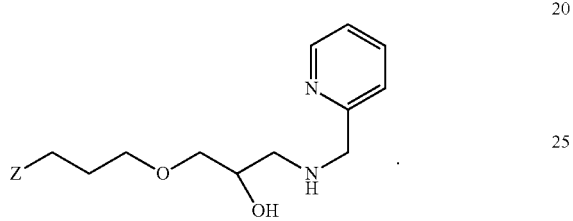

* * * * *